(12) United States Patent
Wu

(10) Patent No.: US 9,914,688 B2
(45) Date of Patent: Mar. 13, 2018

(54) OPTICALLY PURE BENZYL-4-CHLOROPHENYL-C-GLUCOSIDE DERIVATIVE

(71) Applicant: XUANZHU PHARMA CO., LTD., Jinan (CN)

(72) Inventor: Frank Wu, Jinan (CN)

(73) Assignees: SIHUAN PHARMACEUTICAL HOLDINGS GROUP LTD. (CN); XUANZHU PHARMA CO., LTD. (CN)

(*) Notice: Subject to any disclaimer, the term of this patent is extended or adjusted under 35 U.S.C. 154(b) by 0 days.

(21) Appl. No.: 15/067,993

(22) Filed: Mar. 11, 2016

(65) Prior Publication Data

US 2016/0194264 A1 Jul. 7, 2016

Related U.S. Application Data

(62) Division of application No. 14/146,838, filed on Jan. 3, 2014, now Pat. No. 9,315,438.

(51) Int. Cl.
| | |
|---|---|
| C07C 43/247 | (2006.01) |
| A61K 31/351 | (2006.01) |
| C07D 309/10 | (2006.01) |
| A61K 31/403 | (2006.01) |
| A61K 31/155 | (2006.01) |
| A61K 31/4985 | (2006.01) |
| A61K 45/06 | (2006.01) |
| A61K 31/7004 | (2006.01) |

(52) U.S. Cl.
CPC .......... *C07C 43/247* (2013.01); *A61K 31/155* (2013.01); *A61K 31/351* (2013.01); *A61K 31/403* (2013.01); *A61K 31/4985* (2013.01); *A61K 31/7004* (2013.01); *A61K 45/06* (2013.01); *C07D 309/10* (2013.01); *C07C 2602/18* (2017.05)

(58) Field of Classification Search
CPC .... C07C 43/247; A61K 31/351; C07D 309/10
See application file for complete search history.

(56) References Cited

U.S. PATENT DOCUMENTS

| | | | |
|---|---|---|---|
| 5,558,287 A | 9/1996 | Darsey et al. | |
| 6,414,126 B1 | 7/2002 | Ellsworth et al. | |
| 6,515,117 B2 | 2/2003 | Ellsworth et al. | |
| 7,566,699 B2 | 7/2009 | Fushimi et al. | |
| 7,579,449 B2 | 8/2009 | Eckhardt et al. | |
| 7,973,012 B2 | 7/2011 | Kakinuma et al. | |
| 9,562,029 B2 | 2/2017 | Wu | |
| 2004/0082779 A1 | 4/2004 | Vos et al. | |
| 2005/0209166 A1 | 9/2005 | Eckhardt et al. | |
| 2006/0247179 A1 | 11/2006 | Fushimi et al. | |
| 2006/0258749 A1 | 11/2006 | Eckhardt et al. | |
| 2007/0104976 A1 | 5/2007 | Iwakuma et al. | |
| 2007/0238866 A1 | 10/2007 | Deshpande et al. | |
| 2008/0058379 A1 | 3/2008 | Eckhardt et al. | |

(Continued)

FOREIGN PATENT DOCUMENTS

| | | |
|---|---|---|
| CN | 1407990 | 4/2003 |
| CN | 1784415 A | 6/2006 |

(Continued)

OTHER PUBLICATIONS

U.S. Appl. No. 14/129,316, Final Office Action, dated Apr. 27, 2016, 13 pages.
U.S. Appl. No. 14/129,316, Non-Final Office Action, dated Nov. 3, 2015, 13 pages.
U.S. Appl. No. 14/146,838, Non-Final Office Action, dated Jul. 29, 2015, 23 pages.
U.S. Appl. No. 14/146,838, Notice of Allowance, dated Feb. 11, 2016, 17 pages.
Buu-Hoi, et al., 3-Bromo-4-hydroxybiphenyl, Bulletin De La Societe Chimique De France, vol. 2, 1960, pp. 335-337.
EP12805011.9, Extended European Search Report, dated Nov. 3, 2014, 10 pages.

(Continued)

*Primary Examiner* — Jonathan S Lau
(74) *Attorney, Agent, or Firm* — Kilpatrick Townsend & Stockton LLP

(57) ABSTRACT

The present invention belongs to the field of pharmaceutical technology, more specifically relates to optically pure benzyl-4-chlorophenyl-C-glucoside derivatives represented by formulae (II) and (III), a process for preparing these compounds and intermediates thereof, a pharmaceutical formulation and a pharmaceutical composition containing these compounds, and the use of the optically pure benzyl-4-chlorophenyl-C-glucoside derivative as a sodium glucose co-transporter (SGLT) inhibitor in manufacture of a medicament for treating and/or preventing diabetes mellitus (including insulin-dependent diabetes mellitus and non-insulin-dependent diabetes mellitus) or diabetes-associated diseases (including insulin resistance disease and obesity)

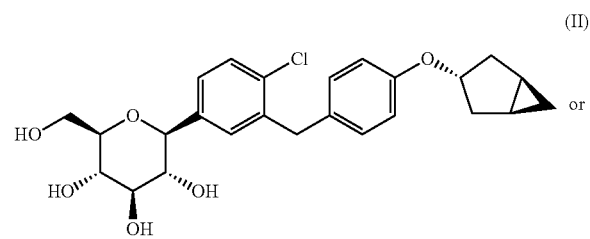

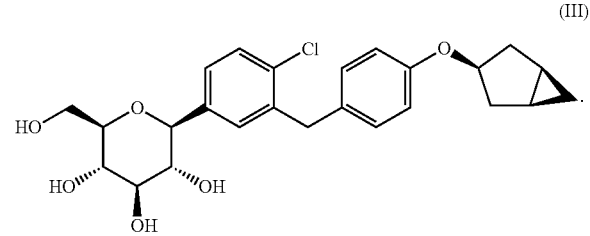

2 Claims, No Drawings

(56) References Cited

U.S. PATENT DOCUMENTS

| | | | |
|---|---|---|---|
| 2009/0118201 A1 | 5/2009 | Chen et al. |
| 2010/0022460 A1 | 1/2010 | Kakinuma et al. |
| 2010/0171418 A1 | 7/2010 | Kinoshita et al. |
| 2013/0022587 A1 | 1/2013 | Nagata et al. |
| 2014/0128331 A1 | 5/2014 | Wu |
| 2015/0191502 A1 | 7/2015 | Wu |
| 2017/0101388 A1 | 4/2017 | Wu |

FOREIGN PATENT DOCUMENTS

| | | |
|---|---|---|
| CN | 1930141 A | 3/2007 |
| CN | 101490028 A | 7/2009 |
| CN | 101790311 A | 7/2010 |
| EP | 725031 A1 | 8/1996 |
| EP | 1696708 A1 | 8/2006 |
| JP | 2000149320 A | 5/2000 |
| JP | 2003511458 A | 3/2003 |
| JP | 2004196788 A | 7/2004 |
| JP | 2006516257 A | 6/2006 |
| JP | 2007522143 A | 8/2007 |
| JP | 2008540489 A | 11/2008 |
| JP | 2009531291 A | 9/2009 |
| KR | 1020110065978 A | 6/2011 |
| TW | 200846441 A | 12/2008 |
| WO | 03035650 A1 | 5/2003 |
| WO | 2005092877 A1 | 10/2005 |
| WO | 2010147430 A2 | 12/2010 |
| WO | 2011115064 A1 | 9/2011 |
| WO | 2012025857 A1 | 3/2012 |
| WO | 2013000275 A1 | 1/2013 |

OTHER PUBLICATIONS

EP14000018.3, Extended European Search Report, dated May 13, 2014, 5 pages.
Guo, et al., Pd(II)-Catalyzed Ortho Arylation of 6-Arylpurines with Aryl Iodides via Purine-Directed C—H Activation: A New Strategy for Modification of 6-Arylpurine Derivatives, Organic letters, vol. 13, No. 8, Mar. 24, 2011, pp. 2008-2011.
JP2014-043695, Office Action, dated Dec. 22, 2015, 4 pages.
JP2014-517397, Office Action, dated May 5, 2015, 3 pages.
Kawano, et al., Preparation of furo[2,3-h] isoquinoline derivatives as viral entry inhibitors against HIV, Atabase Caplus, Chemical Abstracts Service, 2003, 2 pages.
Lansdell, et al., Design and Synthesis of Fluorescent SGLT2 Inhibitors, Bioorg Med Chem Lett, vol. 18, No. 18, Sep. 15, 2008, pp. 4944-4947.
Mansfield, et al., Single-enantiomer drugs: elegant science, disappointing effects, Clin. Pharmacokinet., vol. 43, No. 5, 2004, pp. 287-290.
PCT/CN2012/000868, International Search Report and Written Opinion, dated Oct. 4, 2012, 17 pages.
Yang, Building predictive models for protein tyrosine phosphatase 1B inhibitors based on discriminating structural features by reassembling medicinal chemistry building blocks, Journal of medicinal chemistry, vol. 47, No. 24, Nov. 18, 2004, pp. 5984-5994.
U.S. Appl. No. 14/129,316, Notice of Allowance dated Sep. 22, 2016, 21 pages.
U.S. Appl. No. 14/129,316, Restriction Requirement dated Aug. 10, 2015, 12 pages.

OPTICALLY PURE BENZYL-4-CHLOROPHENYL-C-GLUCOSIDE DERIVATIVE

PRIOR RELATED APPLICATIONS

This application is a divisional application of U.S. application Ser. No. 14/146,838 filed Jan. 3, 2014, which is incorporated herein by reference in its entirety.

FIELD

The present invention belongs to the field of pharmaceutical technology, more specifically relates to optically pure benzyl-4-chlorophenyl-C-glucoside derivatives or pharmaceutically acceptable salts thereof, a process for preparing these compounds and intermediates thereof, a pharmaceutical formulation and a pharmaceutical composition containing these compounds, and the use of optically pure benzyl-4-chlorophenyl-C-glucoside derivatives or pharmaceutically acceptable salts thereof as sodium glucose co-transporter (SGLT) inhibitor in manufacture of a medicament for treating and/or preventing diabetes mellitus (including insulin-dependent diabetes mellitus and non-insulin-dependent diabetes mellitus) or diabetes-associated diseases (including insulin resistance disease and obesity).

BACKGROUND

About 100,000,000 people have the Type II diabetes mellitus all over the world, which is characterized in hyperglycemia caused by excessive hepatic glucose production and peripheral insulin resistance. The hyperglycemia is considered to be a major risk factor for forming the diabetic complication, and be possibly directly relevant to insulin secretion impairment in the later stage of Type II diabetes mellitus. Therefore, it can be expected that the normalization of insulin can improve the blood glucose in the patients having the Type II diabetes mellitus. The currently known anti-diabetic drugs are mostly insulin secretagogues or euglycemic agents, such as sulfonylureas, glinides, thiazolidinediones and dimethyl biguanides, which have potential side effects such as being apt to increase the body weight, hypoglycemia and lactate acidosis, and therefore there is an urgent need to develop a safe and effective anti-diabetic drug having a new mechanism of action.

In kidney, glucose can filter freely through renal glomerulus (about 180 g/d) but nearly transport actively at proximal convoluted tubule to be reabsorbed. Among others, two sodium-glucose transporters, i.e. SGLT-1 and SGLT-2, have an important effect on the glucose reabsorption, in particular SGLT-2. SGLT-2 is a transmembrane protein only specifically expressed at the S1 section of proximal tubule. One of its major physiological functions is to absorb the glucose in the blood flowing through the renal tubule, which comprises 90% of the reabsorption. SGLT-2 transports at a ratio of 1:1 sodium-glucose. The SGLT-2 inhibitor can inhibit the absorption of blood glucose in the renal tubule so that a great amount of glucose excretes through the urine. SGLT-1 mainly expresses in the distal convoluted tubule, which comprises 10% of the reabsorption. SGLT-1 transports at a ratio of 2:1 sodium-glucose. In addition, SGLT-1 is also found in the intestinal tract and other tissues. These transporters exert their functions via Na+/ATPase pump and transport to the blood via the glucose transporter-2 (GLUT2). This indicates that the most potential drug target is the SGLT-2 transporter, because its absolute re-absorption for glucose in one hand and its merely expression in kidney in the other hand. In the study on the urine glucose from the nephrosis of the familial form, the feasibility of this route has been verified. The urine glucose from the nephrosis of the familial form is mainly manifested as non-quantitative urine glucose (about 10-120 g/d), but the patient has a good general condition and has no chronic negative effect adverse for the health to be found. This benign urine glucose is mainly caused by the genic mutation of the SGLT-2 transporter, which indicates that the selective pharmacological inhibition to SGLT-2 will not produce an adverse effect except for the induction of urine glucose. It has been evidenced that one important clinic advantage for the SGLT-2 inhibitor is the low possibility of hypoglycemia. However, the inhibition of SGLT-1 will cause the glucose-galactose malabsorption syndrome, which may result in the dehydration. In addition, it has also been evidenced that the SGLT-1 inhibitor will defer the absorption of carbohydrates and cause a gastrointestinal symptom that is difficult for an individual to tolerate. A highly selective SGLT-2 inhibitor will not block the action of SGLT-1 absorbing the glucose in the intestinal tract transport, and therefore is not apt to cause the gastrointestinal symptom. In addition, SGLT-1 is also highly expressed in the myocardial tissue of the human body, the blocking of SGLT-1 will possibly cause new or structural disease in the cardiac function. Therefore, the development of a compound having a high selectivity on SGLT-2 has a significant meanings in the research for the drug for treating diabetes mellitus.

Since the SGLT-2 inhibitor acts on SGLT-2 transporter to inhibit the reabsorption of the kidney glucose to treat the high blood glucose, a new route for treating the diabetes mellitus is provided. Although this route cannot directly act on the pathophysiology of Type II diabetes mellitus, however the reduction of blood glucose by increasing the excretion of glucose in kidney can cause the deficiency in the net energy to promote losing the body weight and indirectly improve the obesity conditions. It is found in the study that these drugs, if being used in combination of the existing drug for reducing the blood glucose or the insulin, have a lower risk of the hypoglycemia and a potential effect of losing the weight. The SGLT-2 inhibitor is independent on the function of β-cells and the insulin resistance, therefore it is not only effective for a patient having a general diabetes mellitus, but also has a better therapeutic effect for a patient who has experienced a failed treatment with the drugs such as biguanides and DPP-4 inhibitors. Accordingly, the SGLT-2 inhibitor can be used in combination with the hypoglycemic drug such as biguanides and DPP-4 inhibitors in future.

Among others, the patent literatures such as WO 0127128 and US 2005209166 disclose a series of compounds as SGLT-2 inhibitor.

The present applicant also disclosed a series of C-glucoside derivatives as SGLT-2 inhibitor in the PCT application WO2013/000275A1, in which the compound 4 had a good inhibition effect on SGLT-2 and a good selectivity, and had the following structure:

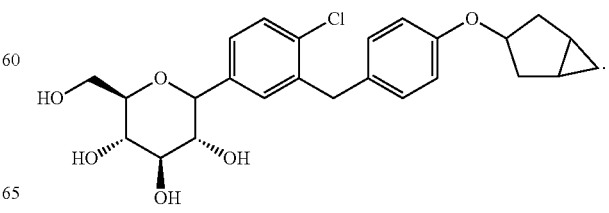

The compound 4 is a mixture of stereoisomers and has asymmetric centers. Therefore, several optical isomers are present. Considering that many chiral mixture drugs in the prior art have the potential problems such as the toxicity and the side effect that are easily produced and unknown, the reduced drug effectiveness, and the difficulty in the quality controlling, the risks for the research and development of the chiral mixture drug will increase remarkably. Since in comparison with the chiral mixture, the optical pure stereoisomer has the advantages such as being more safe, a lower probability of producing the toxicity and the side effect, a better stability, and the ease for quality controlling, and the optical pure stereoisomer also has the characteristics of the potential improvements in the pharmacodynamics, pharmacokinetics and toxicology, therefore the development of a single stereoisomer having high selectivity on SGLT-2, rapid onset, high effectiveness, good safety and good stability has a significant meanings in the subsequent pharmaceutical research and development and the quality controlling in the production of the marketed drug.

SUMMARY

The present invention provides the following technical solutions:

1. A stereoisomeric compound of the compound represented by formula (I) or a pharmaceutically acceptable salt thereof, wherein said stereoisomeric compound is selected from formulae (II), (III), (IV) and (V):

(I)

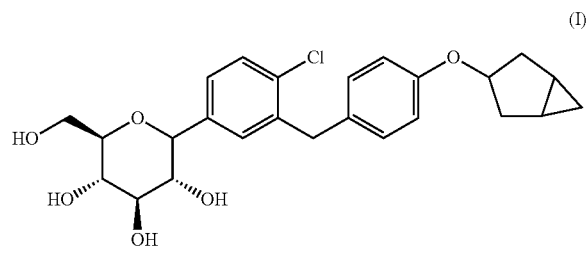

(II)

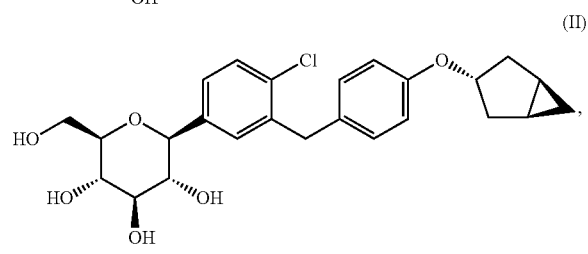

which is (2S,3R,4R,5S,6R)-2-(3-(4-(((1R,3s,5S)-bicyclo [3.1.0]hexan-3-yl)oxy)benzyl)-4-chlorophenyl)-6-(hydroxymethyl)tetrahydro-2H-pyran-3,4,5-triol, (III)

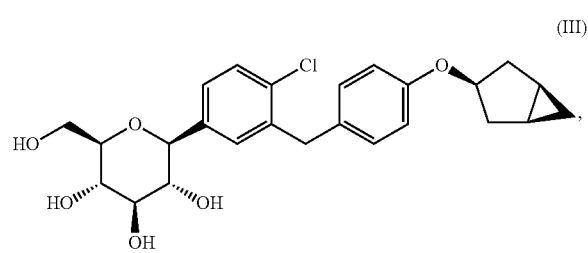 [SMILES: OC[C@H]1O[C@@H](c2ccc(Cl)c(Cc3ccc(O[C@@H]4C[C@@H]5C[C@@H]5C4)cc3)c2)[C@H](O)[C@@H](O)[C@@H]1O]

which is (2S,3R,4R,5S,6R)-2-(3-(4-(((1R,3r,5S)-bicyclo [3.1.0]hexan-3-yl)oxy)benzyl)-4-chlorophenyl)-6-(hydroxymethyl)tetrahydro-2H-pyran-3,4,5-triol, (IV)

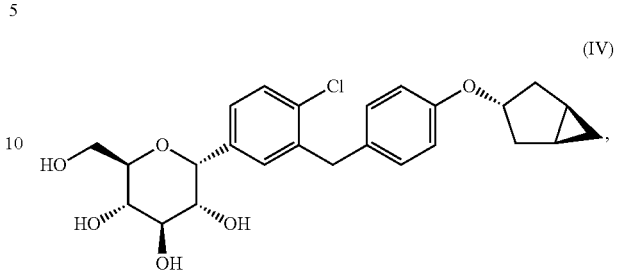

which is (2R,3R,4R,5S,6R)-2-(3-(4-(((1R,3s,5S)-bicyclo [3.1.0]hexan-3-yl)oxy)benzyl)-4-chlorophenyl)-6-(hydroxymethyl)tetrahydro-2H-pyran-3,4,5-triol, (V)

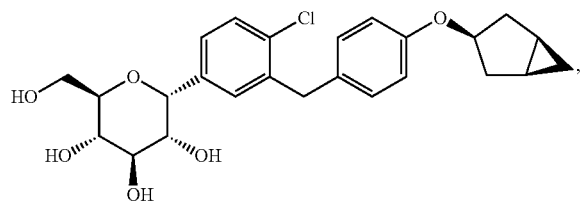

which is (2R,3R,4R,5S,6R)-2-(3-(4-(((1R,3r,5S)-bicyclo [3.1.0]hexan-3-yl)oxy)benzyl)-4-chlorophenyl)-6-(hydroxymethyl)tetrahydro-2H-pyran-3,4,5-triol.

2. A process for preparing the compound represented by formula (II) as defined in technical solution 1, which process comprises the following steps:

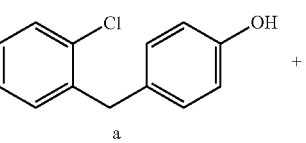

a

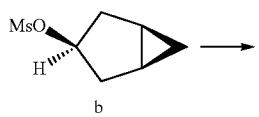

b

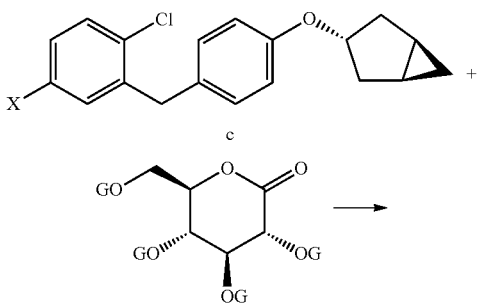

c

-continued

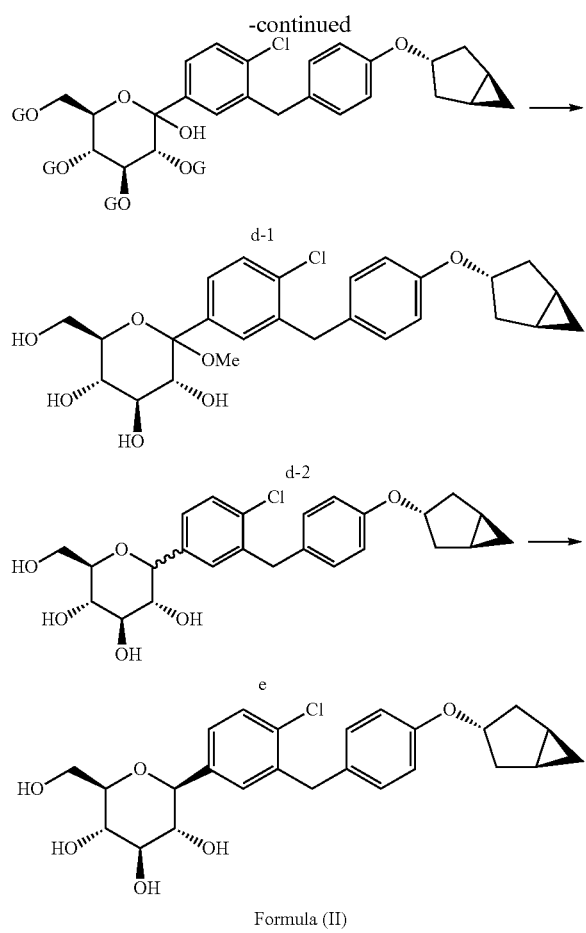

Formula (II)

wherein X represents fluoro, chloro, bromo or iodo,
G represents a hydroxy protecting group, selected from trimethylsilyl, triethylsilyl, benzyl, para-methoxybenzyl, para-nitrobenzyl, pivaloyl, allyl, methoxymethyl, benzyloxymethyl, trimethylsilylethyl and the like, preferably trimethylsilyl.

The steps comprise:
a compound of formula b (i.e. (1R,3r,5S)-bicyclo[3.1.0] hexan-3-yl methanesulfonate) is dissolved in an organic solvent (which can be selected from N-methylpyrrolidone, N,N-dimethylformamide, tetrahydrofuran, dioxane and acetonitrile, preferably N-methylpyrrolidone); to the resulting mixture is added a compound of formula a; and then the resulting mixture is reacted at a temperature between 0° C. and 70° C. to produce a compound of formula c;
the compound of formula c is reacted with

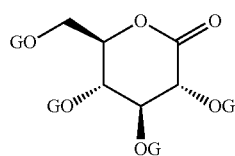

to produce a compound of formula d-1, which is deprotected to produce a compound of formula d-2;
the compound of formula d-2 is reacted at a temperature between −78° C. and 30° C. to produce a compound of formula e; and the compound of formula e is purified to produce the compound represented by formula (II).

The compound of formula e, as mentioned above, can be purified to produce the compound represented by formula (II), for example, according to the following method:
the compound of formula e is subjected to a hydroxy protection reaction to produce a compound of formula f; and
the compound of formula f is subjected to a deprotection reaction to produce the compound represented by formula (II),

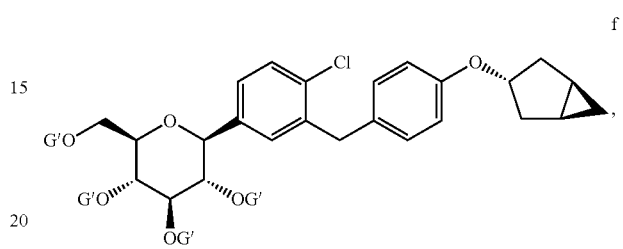

wherein G' represents a hydroxy protecting group, selected from acetyl, trimethylsilyl, triethylsilyl, benzyl, para-methoxybenzyl, para-nitrobenzyl, pivaloyl, allyl, methoxymethyl, benzyloxymethyl, trimethylsilylethyl, propionyl, isobutyryl, benzoyl and the like, preferably acetyl, pivaloyl, propionyl, isobutyryl or benzoyl.

It should be noted that the compound represented by formula (II) can be prepared according to the methods as illustrated in the above scheme and/or according to other technologies well known to a person skilled in the art, however the above methods are not exclusive.

3. A process for preparing the compound represented by formula (III) as defined in technical solution 1, which process comprises the following steps:

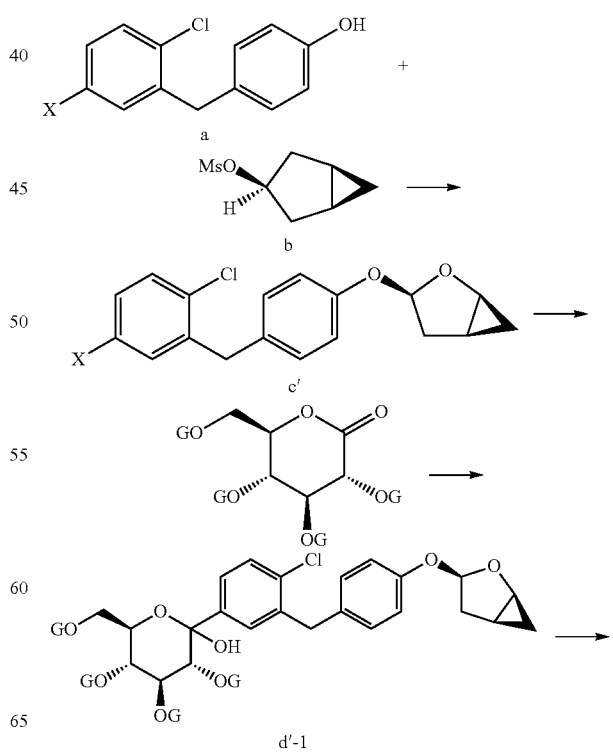

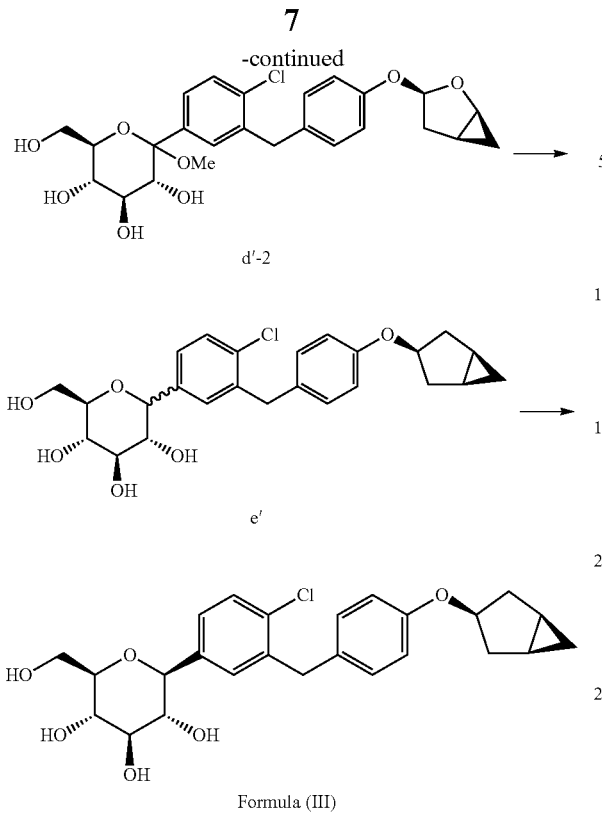

d'-2 e'

Formula (III)

wherein X represents fluoro, chloro, bromo or iodo,
G represents a hydroxy protecting group, selected from trimethylsilyl, triethylsilyl, benzyl, para-methoxybenzyl, para-nitrobenzyl, pivaloyl, allyl, methoxymethyl, benzyloxymethyl, trimethylsilylethyl and the like, preferably trimethylsilyl.

The steps comprise:
a compound of formula a is dissolved in an organic solvent (which can be selected from toluene, N,N-dimethylformamide, tetrahydrofuran, dioxane and acetonitrile, preferably toluene); to the resulting mixture is added a compound of formula b; and then the resulting mixture is reacted at a temperature between 0° C. and 70° C. to produce a compound of formula c';
the compound of formula c' is reacted with

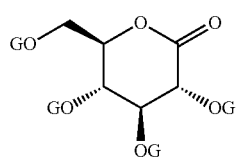

to produce a compound of formula d'-1, which is deprotected to produce a compound of formula d'-2;
the compound of formula d'-2 is reacted at a temperature between −78° C. and 30° C. to produce a compound of formula e'; and
the compound of formula e' is purified to produce the compound represented by formula (III).

The compound of formula e', as mentioned above, can be purified to produce the compound represented by formula (III), for example, according to the following method:
the compound of formula e' is subjected to a hydroxy protection reaction to produce a compound of formula f'; and the compound of formula f' is subjected to a deprotection reaction to produce the compound represented by formula (III),

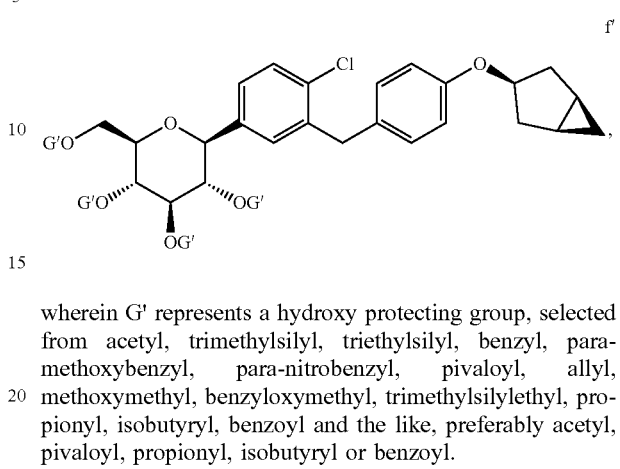

f' wherein G' represents a hydroxy protecting group, selected from acetyl, trimethylsilyl, triethylsilyl, benzyl, para-methoxybenzyl, para-nitrobenzyl, pivaloyl, allyl, methoxymethyl, benzyloxymethyl, trimethylsilylethyl, propionyl, isobutyryl, benzoyl and the like, preferably acetyl, pivaloyl, propionyl, isobutyryl or benzoyl.

It should be noted that the compound represented by formula (III) can be prepared according to the methods as illustrated in the above scheme and/or according to other technologies well known to a person skilled in the art, however the above methods are not exclusive.

4. An intermediate for the compound represented by formula (II), wherein said intermediate is

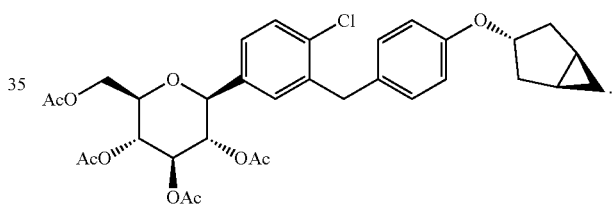

5. An intermediate for the compound represented by formula (II), wherein said intermediate is

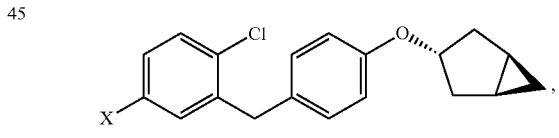

wherein X represents bromo or iodo.

6. An intermediate for the compound represented by formula (III), wherein said intermediate is

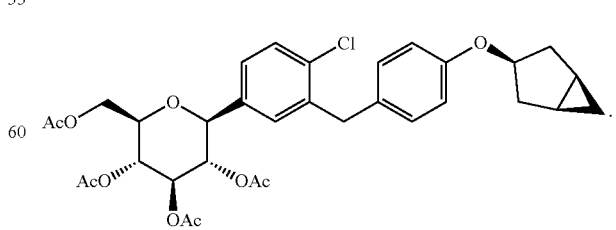

7. An intermediate for the compound represented by formula (III), wherein said intermediate is

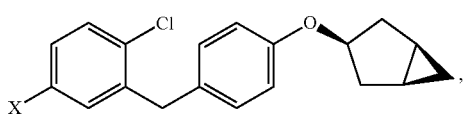

wherein X represents bromo or iodo.

As used herein, said "pharmaceutically acceptable salt" comprises alkali metal salts, such as Na salt, K salt, Li salt and the like; alkaline-earth metal salts, such as Ca salt, Mg salt and the like; other metal salts, such as Al salt, Fe salt, Zn salt, Cu salt, Ni salt, Co salt and the like; inorganic base salts, such as ammonium salt; organic base salts, such as tert-octylamine salt, dibenzylamine salt, morpholine salt, glucosamine salt, phenyl glycine alkyl ester salt, ethylene diamine salt, N-methylglucosamine salt, guanidine salt, diethylamine salt, triethylamine salt, dicyclohexyl amine salt, N,N'-dibenzylethylene diamine salt, chloroprocaine salt, procaine salt, diethanol amine salt, N-benzyl-phenyl-ethyl amine salt, piperazine salt, tetramethyl amine salt, tris(hydroxymethyl)aminomethane salt and the like; halogen acid salt, such as hydrofluoric acid salt, hydrochloride, hydrobromide, hydriodate and the like; inorganic acid salts, such as nitrate, perchlorate, sulfate, phosphate and the like; lower alkanesulfonate, such as mesylate, trifluoromesylate, ethanesulfonate and the like; arylsulfonate, such as benzenesulfonate, para-benzenesulfonate and the like; organic acid salts, such as acetate, malate, fumarate, succinate, citrate, tartrate, oxalate, maleate and the like; amino acid salts, such as glycine salt, trimethyl glycine salt, arginine salt, ornithine salt, glutamate salt, aspartate salt and the like.

The present invention also involves a pharmaceutical composition, which contains the compound represented by formula (II) and/or the compound represented by formula (III) or a pharmaceutically acceptable salt thereof, and one or more pharmaceutically acceptable carriers and/or diluents, and can be prepared into any pharmaceutically acceptable dosage form. The pharmaceutical composition can be administered orally, parenterally, rectally or pulmonarily to a patient in need thereof. For the oral administration, it can be prepared into a conventional solid formulation, such as tablet, capsule, pill, granule and the like; or into an oral liquid formulation, such as oral solution, oral suspension, syrup and the like. Upon preparing into an oral formulation, suitable filler, binder, disintegrant, lubricant and the like can be added. For the parenteral administration, it can be prepared into an injectable preparation, including an injection solution, a sterile injection powder and a concentrated injection solution. For preparing the injectable preparation, an additive can be optionally added, depending on the nature of drug. For the rectal administration, it can be prepared into a suppository and the like. For the pulmonary administration, it can be prepared into an inhalant, a spraying agent and the like. Per unit of the formulation contains a physiologically effective amount, for example 0.005 g-10 g, such as 0.005 g, 0.01 g, 0.05 g, 0.1 g, 0.125 g, 0.2 g, 0.25 g, 0.3 g, 0.4 g, 0.5 g, 0.6 g, 0.75 g, 1 g, 1.25 g, 1.5 g, 1.75 g, 2 g, 2.5 g, 3 g, 4 g, 5 g, 10 g and the like of the compound represented by formula (II) and/or the compound represented by formula (III) or a pharmaceutically acceptable salt thereof.

The present invention also involves a pharmaceutical combination, which contains the compound represented by formula (II) and/or the compound represented by formula (III) or a pharmaceutically acceptable salt thereof, and other pharmaceutically active component(s). Said other pharmaceutically active component can be one or more hypoglycemic agents. Said hypoglycemic agent can be selected from sitagliptin phosphate, vildagliptin, saxagliptin, alogliptin benzoate, linagliptin, teneligliptin, gemigliptin, metformin, phenformin, exenatide, liraglutide and the like.

The present invention also involves the use of the compound represented by formula (II) and/or the compound represented by formula (III) or a pharmaceutically acceptable salt thereof in manufacture of a medicament for treating and/or preventing diabetes mellitus or diabetes-associated diseases. Said diabetes mellitus includes insulin-dependent diabetes mellitus (Type I) and non-insulin-dependent diabetes mellitus (Type II). Said diabetes-associated disease includes insulin resistance disease, obesity and the like.

The present invention also involves a method for treating and/or preventing diabetes mellitus (including insulin-dependent diabetes mellitus and non-insulin-dependent diabetes mellitus) or diabetes-associated diseases (including insulin resistance disease and obesity) in a mammal (including a human) in need thereof, which method comprises administering to such mammal a therapeutically effective amount of the compound represented by formula (II) and/or the compound represented by formula (III) or a pharmaceutically acceptable salt thereof.

The compound of the present invention has the following characteristics:

(1) The compound of the present invention has a high selectivity for SGLT-2, and can be safely used to treat and/or prevent diabetes mellitus or diabetes-associated diseases in a mammal (including a human) in need thereof.

(2) The compound of the present invention has a highly-effective inhibition on SGLT-2 and a remarkable hypoglycemic activity, a rapid onset, a low toxicity and a low side-effect, and a high safety.

(3) The compound of the present invention has a good physical-chemical property, a high purity, a good stability and a easily-controllable quality, and is apt to be produced industrially on a large scale.

DETAILED DESCRIPTION

For convenience, the well-known abbreviations that are used in the present description include:
Me: methyl;
Et: ethyl;
Ms: methylsulfonyl;
Ac: acetyl;
TBS: tert-butyldimethylsilyl;
THF: tetrahydrofuran;
DMAP: 4-dimethylaminopyridine;
DIPEA: N,N-diisopropylethylamine;
n-BuLi: n-butyl lithium;
TMS: trimethylsilyl.

In the present invention, room temperature means a temperature between 10° C. and 30° C.

Hereinafter, the beneficial effects of the present compounds will be illustrated with the assays for the pharmacological activities. However, it should be noted that the beneficial effects of the present compounds are not limited to the effects as illustrated below.

Assay 1: An In-Vitro Assay for the Pharmacological Activities of the Present Compounds Assay samples: Compounds represented by formulae (II), (III), (IV) and (V) as defined hereinbefore, lab-made, their chemical names and preparation processes are described in the following preparation examples.

Reference compound 1: Compound 4 as described in the PCT application WO2013/000275A1, lab-made (with reference to the PCT application WO2013/000275A1), its structure is as follows:

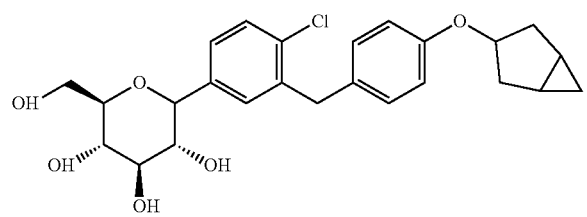 [SMILES: OC[C@H]1OC(c2ccc(Cl)c(Cc3ccc(OC4CC5CC5C4)cc3)c2)[C@H](O)[C@@H](O)[C@@H]1O]

Compound 4, i.e. the compound represented by formula (I).

The abbreviation(s) used in the following assay has the following meanings:

NMG N-methyl-glucosamine
KRH Krebs-Ringer-Henseleit

In the in-vitro assay for the pharmacological activities of the present compounds, the human SGLT-2 and SGLT-1 sequences were transfected to Chinese hamster ovary cells to express stably. By measuring inhibition of the sodium dependent adsorption of [$^{14}$C]-labeled R-methyl-D-glucopyranoside (AMG) into the cells, the half-inhibition concentration $IC_{50}$ was determined.

Buffer A (KRH-Na$^+$): 120 mM NaCl, 4.7 mM KCl, 1.2 mM MgCl$_2$, 2.2 mM CaCl$_2$, 10 mM HEPES (PH 7.4 with 1 mM Tris).

Buffer A– (KRH-NMG): 120 mM NMG, 4.7 mM KCl, 1.2 mM MgCl$_2$, 2.2 mM CaCl$_2$, 10 mM HEPES (PH 7.4 with 1 mM Tris).

Buffer D: 120 mM NaCl, 4.7 mM KCl, 1.2 mM MgCl$_2$, 2.2 mM CaCl$_2$, 10 mM HEPES, 0.5 mM phlorizin (PH 7.4 with 1 mM Tris).

Assay method: Human SGLT-2 and SGLT-1 sequences were stably expressed in the CHO cells. The cell culture was conducted in a 96-well plate for 12 hr. The plate was washed with KRH-Na+ (Buffer A) or KRH-NMG (Buffer A–) buffering solution for three times, 200 μL/well. Then the plate was added with a buffering solution containing Buffer A or Buffer A– plus [$^{14}$C]-AMG (10 μCi/mL), 100 μL/well. The cell culture was conducted at 37° C. for 1 hr. Then, 100 μL of an ice pre-cooled buffering solution (Buffer D) was added to terminate the assay. The plate was washed for five times. Then an ice pre-cooled lytic buffering solution (100 mM NaOH solution) was added, 20 μL/well, and the centrifugation at 600 rpm was conducted for 5 mins. Then Microscint 40 solution was added, 80 μl/well, and the centrifugation at 600 rpm was conducted for 5 mins. Finally, the radioactivity of [$^{14}$C]-AMG was detected with Micro-Beta Trilux (purchased from PerkinElmer Co. Ltd.) according to the scintillation counting method, and the half-inhibition concentration $IC_{50}$ was calculated.

Assay Results and Conclusions:

TABLE 1

The inhibition effects of the present compounds

| Nos. | SGLT-1 $IC_{50}$(nM) | SGLT-2 $IC_{50}$(nM) | Selectivity |
|---|---|---|---|
| Reference compound 1 | 2397.69 | 3.63 | 660.52 |
| Compound represented by formula (II) | 17217.33 | 2.50 | 6886.93 |
| Compound represented by formula (III) | 3075.36 | 7.83 | 392.77 |
| Compound represented by formula (IV) | 111470.59 | 1110.95 | 100.34 |
| Compound represented by formula (V) | 75465.18 | 281.83 | 267.77 |

It was seen from the above table 1 that the compound represented by formula (II) according to the present invention had a better inhibition effect on SGLT-2 as well as a better selectivity than the reference compound 1, and showed a remarkable advantage.

Assay 2: Rat In-Vivo Pharmacokinetic Assay for the Present Compounds

Assay animals: 6-8 weeks aged male SD rats (purchased from Vital River Laboratories), 3 rats per compound, weighing 200-240 g.

Assay samples: The compound represented by formula (II) as defined hereinbefore, lab-made, its chemical name and preparation process are described in the following Example 1. Reference compound 1: Compound 4 as described in the PCT application WO2013/000275A1, lab-made (with reference to the PCT application WO2013/000275A1), its structure is as follows:

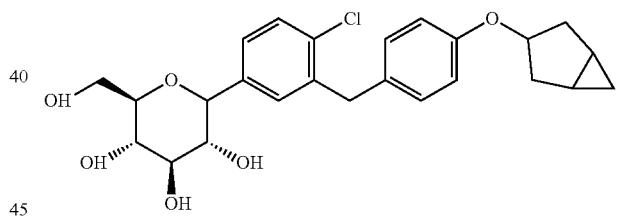

Compound 4, i.e. the compound represented by formula (I).

Reference compound 2: Compound 22 as described in the PCT application WO2013/000275A1, lab-made (with reference to the PCT application WO2013/000275A1), its structure is as follows:

Compound 22

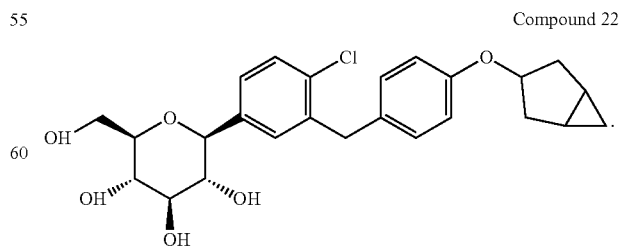

Solvent: 0.5% MC (methyl cellulose) solution+0.1% SDS (sodium dodecyl sulfate).

Assay Method:
Intragastric administration (PO): See Table 2

TABLE 2

Administration of compounds in the rat PK (pharmacokinetic) assay

| Animal amount | Sex | Route | Dosage (mg/kg) | Volume (ml/kg) | Concentration (mg/mL) |
|---|---|---|---|---|---|
| 3 | Male | PO | 10 | 5 | 2 |

Blood collection: each of 200 μL whole blood were collected at 0.17 hr, 0.5 hr, 1 hr, 2 hr, 4 hr, 6 hr, 8 hr, 24 hr, 30 hr, 48 hr, 54 hr and 72 hr. The collected blood samples were centrifuged at 4° C. at 8000 rpm in a low temperature high-speed centrifuge (5415R, Eppendorf) for 6 mins to separate the blood plasma. The separated plasma was preserved at −80° C. in a refrigerator.

Plasma Sample Analysis:

20 μL of the plasma was carefully taken out, to which was added 600 μL of an internal standard MTBE (methyl tert-butyl ether) solution (containing internal standard dapagliflozin 25 ng/ml). The plasma was subjected to a vortex at 1500 rpm for 10 mins, and then centrifuged at 12000 rpm for 5 mins. 400 μL of the supernatant was taken and blow-dried with nitrogen gas. The dried substance was redissolved with 200 μL of a redissolving solution (acetonitrile:water=7:3). The solution was subjected to a vortex for 10 mins, and analyzed with LC-MS/MS (API4000, Applied Biosystems).

TABLE 3

Rat PK (pharmacokinetic) evaluation results (PO) for the compounds

| | PK parameters (units) | | | | |
|---|---|---|---|---|---|
| | $T_{1/2}$ (h) | Tmax (h) | Cmax (ng/ml) | $AUC_{last}$ (h*ng/ml) | $AUC_{inf}$ (h*ng/ml) |
| Reference compound 1 | 10.26 | 2 | 4143 | 69582 | 70279 |
| Reference compound 2 | 8.18 | 2 | 4977 | 69297 | 69392 |
| Compound represented by formula (II) | 8.98 | 1 | 6383 | 92064 | 92123 |

$T_{1/2}$ represents the half-life
Tmax represents the time to peak the concentration in the plasma
Cmax represents the peak concentration in the plasma
$AUC_{last}$ represents the area under curve on administration from time = 0→t
$AUC_{inf}$ represents the area under curve on administration from time = 0→∞

CONCLUSION it was seen from the result shown in Table 3 that the compound represented by formula (II) according to the present invention had a short time to peak the concentration in the plasma and a rapid onset. In comparison with reference compound 1 and reference compound 2, the compound represented by formula (II) according to the present invention showed a higher exposure, and had a substantial difference, which demonstrated that the compound represented by formula (II) according to the present invention had a notable progress.

The following preparation examples are intended to illustrate the invention and are not to be construed as being limitations thereon. All of the technical solutions that can be accomplished based on the above disclosure fall in the scope of the present invention.

In the preparation examples, the used starting materials were commercially available, for example, from Alfa Aesar China (Tianjin) Co., Ltd., Sinopharm Chemical Reagent Co., Ltd., Tianjin Fuyu Fine Chemical Co., Ltd., Shanghai Bangchen Chemical Co. Ltd., Tianjin Guangcheng Chemical Reagent Co., Ltd., Tianjin Guangfu Fine Chemical Co., Ltd., Tianjin Kemiou Chemical Reagent Co., Ltd.

Example 1

Preparation of (2S,3R,4R,5S,6R)-2-(3-(4-(((1R,3s, 5S)-bicyclo[3.1.0]hexan-3-yl)oxy)benzyl)-4-chlorophenyl)-6-(hydroxymethyl)tetrahydro-2H-pyran-3,4, 5-triol (Formula II)

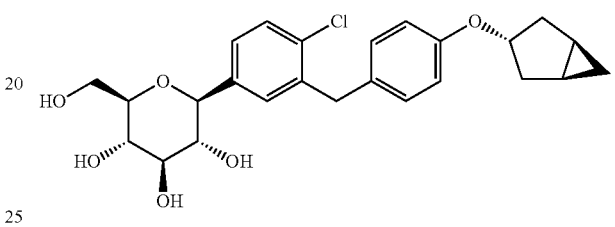

(1) Preparation of 5-bromo-2-chlorobenzoyl chloride

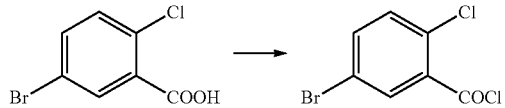 [SMILES: O=C(O)c1cc(Br)ccc1Cl ; O=C(Cl)c1cc(Br)ccc1Cl]

5-bromo-2-chlorobenzoic acid (270 g, 1.15 mol) was suspended in methylene chloride (2700 mL). To the resulting mixture was added N,N-dimethylformamide (1 mL), and then added dropwise oxalyl chloride (288 mL, 3.46 mol) at 0° C. After the completion of dropwise addition, the mixture was warmed up to 20° C. and reacted for 3 h. The reaction mixture became clear, and TLC (Thin layer chromatography) indicated the completion of reaction. The reaction mixture was evaporated by rotation at 30-35° C. to produce a product, which was directly used in the next reaction.

(2) Preparation of (5-bromo-2-chlorophenyl)(4-methoxyphenyl)methanone

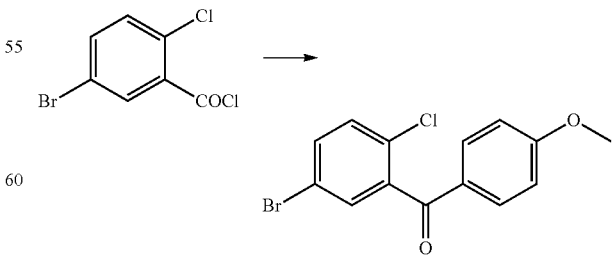

Anhydrous aluminum trichloride (155 g, 1.16 mol) was suspended in methylene chloride (2050 mL) under a nitrogen protection. To the resulting mixture was added anisole (125 mL, 1.15 mol) in one batch at −5° C. After stirring for 20 mins, to the mixture was added dropwise a solution of 5-bromo-2-chlorobenzoyl chloride in methylene chloride (300 mL). The resulting mixture was reacted at −5° C. for 3 h. TLC indicated the completion of reaction. To the reaction mixture was poured 2N hydrochloric acid. The resulting mixture was separated into an organic phase and an aqueous phase. The organic phase was washed with a saturated sodium bicarbonate solution for two times and with a saturated sodium chloride solution, dried over anhydrous sodium sulphate, and evaporated by rotation to produce a solid. To the solid was added ethanol (150 mL), and the resulting mixture was washed and starched for 30 mins and filtered. The filter cake was oven dried to produce 265 g of a product in a yield of 71%.

(3) Preparation of
4-bromo-1-chloro-2-(4-methoxybenzyl)benzene

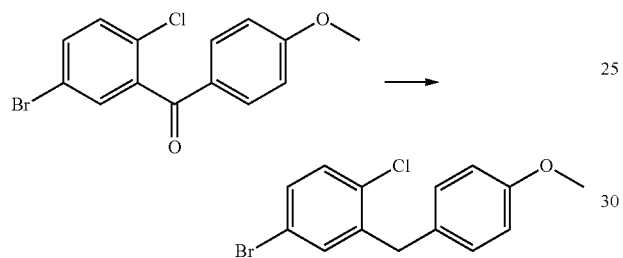

(5-bromo-2-chlorophenyl)(4-methoxyphenyl)methanone (265 g, 0.81 mol) was dissolved in methylene chloride (515 mL) and acetonitrile (1030 mL). To the resulting mixture was added triethyl silane (352 mL, 2.22 mol). Then to the resulting mixture was added dropwise boron trifluoride-diethyl etherate (273 mL, 2.22 mol) at 0° C. under a nitrogen protection. After the completion of dropwise addition, the resulting mixture was stirred for 20 min, warmed up to room temperature and reacted for 2 hr. TLC indicated the completion of reaction. To the reaction mixture were added methyl tert-butyl ether (1.5 L) and a saturated sodium bicarbonate solution (1.5 L). The mixture was stirred for 30 mins. The organic phase was separated off, washed with a saturated sodium bicarbonate solution for four times and with a saturated sodium chloride solution for one time, dried over anhydrous sodium sulphate, and evaporated by rotation to produce an oily substance. To the oily substance was added ethanol. The resulting mixture was stirred at room temperature for 30 mins and in an ice bath for 30 mins. A great quantity of solid was separated out and filtered. The filter cake was dried to produce 226 g of a product in a yield of 89%.

(4) Preparation of
4-(5-bromo-2-chlorobenzyl)phenol

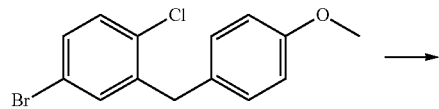

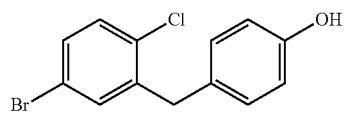

4-bromo-1-chloro-2-(4-methoxybenzyl)benzene (226 g, 0.73 mol) was dissolved in methylene chloride (2240 mL) under a nitrogen protection and in a protection from light. To the resulting mixture was slowly added dropwise a solution of boron tribromide (357 g, 1.42 mol) in methylene chloride (1416 mL) at −78° C. After the completion of dropwise addition, the reaction mixture was warmed up to room temperature and reacted for 2 hr. TLC indicated the completion of reaction. To the reaction mixture was slowly added dropwise water in an ice-water bath. The methylene chloride phase was collected. The residual aqueous phase was extracted with methylene chloride (1 L) for two times. The organic phases were combined, washed with water for two times and with a saturated sodium chloride solution for one time, dried over anhydrous sodium sulphate, and evaporated by rotation to produce 210 g of a product in a yield of 97%.

(5) Preparation of
(1R,3r,5S)-bicyclo[3.1.0]hexan-3-ol

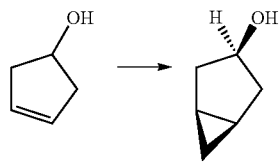 [SMILES: OC1CC=CC1 ; O[C@@H]1C[C@@H]2C[C@@H]2C1]

Diethyl zinc (7.16 L, 7.14 mol) was added dropwise to methylene chloride (9 L) at 0° C. When the white fume disappeared after the completion of dropwise addition, to the resulting mixture was slowly added dropwise a solution of trifluoroacetic acid (816 g, 7.16 mol) in methylene chloride (1 L). After the completion of dropwise addition, the resulting mixture was stirred for 30 mins. To the mixture was added dropwise a solution of methylene iodide (1918 g, 7.14 mol) in methylene chloride (1 L). After the completion of dropwise addition, the resulting mixture was stirred for 30 mins. To the mixture was added dropwise a solution of cyclopent-3-en-1-ol (200 g, 2.38 mol) in methylene chloride (800 mL). After the completion of dropwise addition, the resulting mixture was warmed up to room temperature and reacted for 30 mins. TLC indicated the completion of reaction. The reaction mixture was poured into a saturated ammonium chloride. After stirring for 10 mins, the mixture was separated into an organic phase and an aqueous phase. The aqueous phase was extracted with methylene chloride (2 L) for one time. The organic phase was washed with a saturated sodium sulphite, with a saturated sodium bicarbonate, and with a saturated sodium chloride, and dried over anhydrous sodium sulphate. The residue is purified with a column chromatography to produce 112 g of a product in a yield of 48%.

(6) Preparation of (1R,3r,5S)-bicyclo[3.1.0]hexan-3-yl methanesulfonate

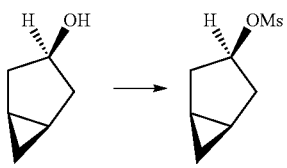 [SMILES: O[C@@H]1C[C@@H]2C[C@@H]2C1 ; CS(=O)(=O)O[C@@H]1C[C@@H]2C[C@@H]2C1]

(1R,3r,5S)-bicyclo[3.1.0]hexan-3-ol (112 g, 1.14 mol) was dissolved in methylene chloride (1250 mL) in an ice-water bath. To the resulting mixture was added triethylamine (174 g, 1.69 mol), and then slowly added dropwise methylsulfonyl chloride (197 g, 1.72 mol). After the completion of dropwise addition, the resulting mixture was reacted for 30 mins at 0° C. TLC indicated the completion of reaction. The reaction mixture was poured into water and separated into an organic phase and an aqueous phase. The organic phase was washed with a diluted hydrochloric acid for one time, with water for two times, and then with a saturated sodium chloride, dried over anhydrous sodium sulphate, and evaporated by rotation to produce 138 g of a product in a yield of 68%.

(7) Preparation of (1R,3s,5S)-3-(4-(5-bromo-2-chlorobenzyl)phenyloxy)bicyclo[3.1.0]hexane

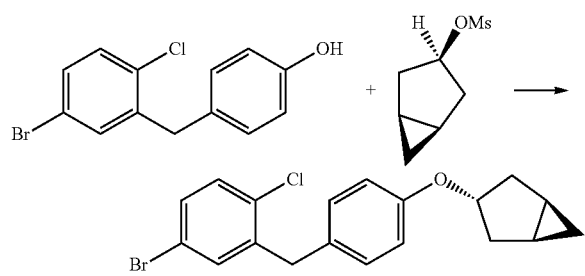

(1R,3r,5S)-bicyclo[3.1.0]hexan-3-yl methanesulfonate (138 g, 0.78 mol) was dissolved in N-methylpyrrolidone (2.1 L). To the resulting mixture was added 4-(5-bromo-2-chlorobenzyl)phenol (210 g, 0.71 mol), cesium carbonate (462 g, 1.42 mol) and benzyltriethylammonium chloride (5.46 g, 24 mmol). Then the resulting mixture was stirred for 10 mins at room temperature, warmed up to 50° C., and reacted overnight. TLC indicated the completion of reaction. To the reaction mixture was added water. Then the resulting mixture was extracted with a mixed solution of petroleum ether and methyl tert-butyl ether (petroleum ether:methyl tert-butyl ether=1:1) for two times. The organic phases were combined, washed with a saturated sodium bicarbonate solution for two times and with a saturated sodium chloride for two times, dried over anhydrous sodium sulphate, and evaporated by rotation. The residue was purified with a column chromatography (petroleum ether:ethyl acetate=50:1) to produce 135 g of the product in a yield of 50%.

Formula: $C_{19}H_{18}BrClO$; Mw: 377.71

$^1$H-NMR (400 MHz, CDCl$_3$) δ: 7.28-7.21 (m, 3H), 7.07-7.05 (d, 2H), 6.82-6.78 (m, 2H), 4.42-4.35 (m, 1H), 3.98 (s, 2H), 2.36-2.31 (m, 2H), 1.96-1.90 (m, 2H), 1.40-1.33 (m, 2H), 0.47-0.44 (m, 1H), 0.07-0.02 (m, 1H).

(8) Preparation of (3R,4S,5R,6R)-3,4,5-tri((trimethylsilyl)oxy)-6-(((trimethylsilyl)oxy)methyl)tetrahydro-2H-pyran-2-one

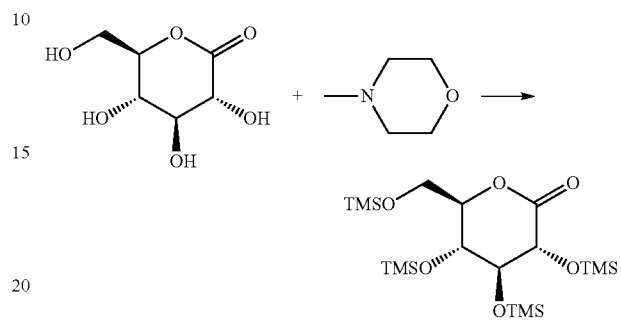

(3R,4S,5S,6R)-3,4,5-trihydroxy-6-(hydroxymethyl)tetrahydro-2H-pyran-2-one (85 g, 0.47 mol) was suspended in THF (tetrahydrofuran) (932 mL). To the resulting mixture was added N-methylmorpholine (405 mL, 4.78 mol). Then the resulting mixture was cooled to −5° C. under a nitrogen protection, and TMSCl (trimethylsilane chloride) (360 mL, 4.78 mol) was added dropwise thereto. After the completion of dropwise addition, the resulting mixture was stirred at room temperature for 1 h and at 35° C. for 5 hr. Then the mixture was stirred overnight while the temperature was maintained at 25° C. TLC indicated the completion of reaction. To the reaction mixture was added toluene (200 mL) and added dropwise water (1 L) in an ice-water bath. The organic phase was collected, washed with sodium dihydrogen phosphate for one time, with water for one time, and with a saturated sodium chloride solution for one time, dried and concentrated to produce 218 g of a product in a yield of 100%.

(9) Preparation of (3R,4S,5S,6R)-2-(3-(4-(((1R,3s,5S)-bicyclo[3.1.0]hexan-3-yl)oxy)benzyl)-4-chlorophenyl)-6-(hydroxymethyl)-2-methoxytetrahydro-2H-pyran-3,4,5-triol

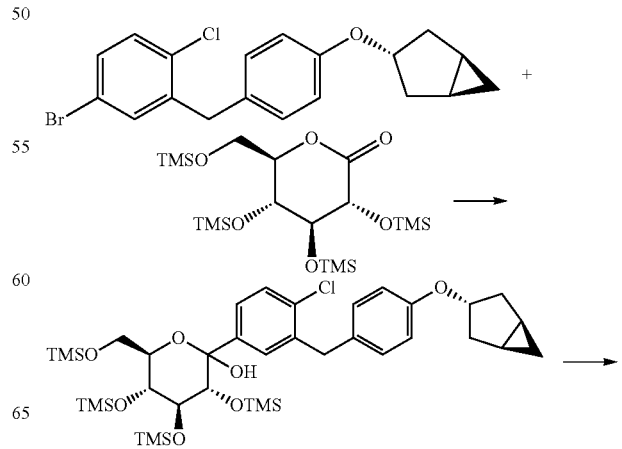

-continued

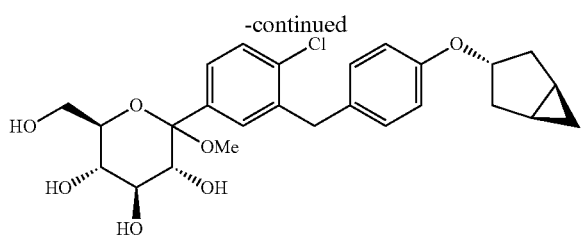

(1R,3s,5S)-3-(4-(5-bromo-2-chlorobenzyl)phenyloxy)bicyclo[3.1.0]hexane (135 g, 0.358 mol) was dissolved in tetrahydrofuran (813 mL) and toluene (813 mL) under a nitrogen protection. The resulting mixture was cooled to −78° C., and n-butyl lithium (194 mL, 0.465 mol) was added dropwise thereto. After the completion of dropwise addition, the reaction mixture was stirred for 2 hr, sucked out with an injector, and then injected to a solution of (3R,4S,5R,6R)-3,4,5-tri((trimethylsilyl)oxy)-6-(((trimethylsilyl)oxy)methyl)tetrahydro-2H-pyran-2-one (218 g, 0.47 mol) in toluene (950 mL). The resulting mixture was stirred for 1 hr, and a solution of methylsulfonic acid (44.9 mL, 2.15 mol) in methanol (1.2 L) was added thereto. The mixture was stirred at −78° C. for 1 hr, warmed up to room temperature, and reacted overnight. TLC indicated the completion of reaction. The reaction mixture was quenched with a saturated sodium bicarbonate solution, and extracted with ethyl acetate (2 L). The organic phase was washed with water and with a saturated sodium chloride solution, dried over anhydrous sodium sulphate, and evaporated by rotation to produce 173 g of a product in a yield of 98%.

(10) Preparation of (3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol

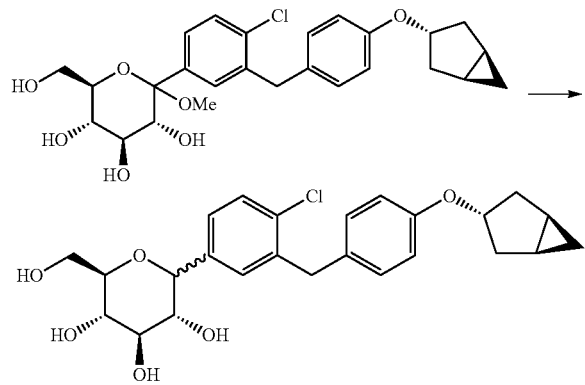

(3R,4S,5S,6R)-2-(3-(4-(((1R,3s,5S)-bicyclo[3.1.0]hexan-3-yl)oxy)benzyl)-4-chlorophenyl)-6-(hydroxymethyl)-2-methoxytetrahydro-2H-pyran-3,4,5-triol (173 g, 0.352 mol) and triethyl silane (180 mL, 1.05 mol) were dissolved in methylene chloride (2 L) at −78° C. in a nitrogen protection. To the resulting mixture was slowly added dropwise boron trifluoride-diethyl etherate (134 mL, 1.05 mol). After the completion of dropwise addition, the mixture was reacted at −78° C. for 1 hr. The reaction mixture was slowly warmed up to room temperature and reacted for 1 hr. HPLC indicated the completion of reaction. To the reaction mixture was added dropwise a saturated sodium bicarbonate solution. The resulting mixture was extracted with ethyl acetate (1 L). The organic phase was washed with water and with a saturated sodium chloride solution, dried over anhydrous sodium sulphate, and evaporated by rotation to produce 143 g of a product in a yield of 88%.

(11) Preparation of (2R,3R,4R,5S,6S)-2-(acetoxymethyl)-6-(3-(4-(((1R,3s,5S)-bicyclo[3.1.0]hexan-3-yl)oxy)benzyl)-4-chlorophenyl)tetrahydro-2H-pyran-3,4,5-triyl triacetate

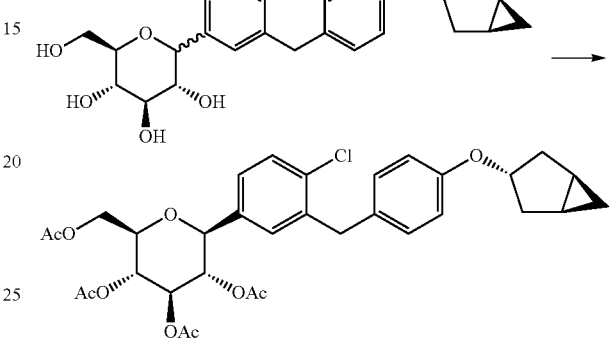

(3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol (143 g, 0.311 mol) was dissolved in methylene chloride (720 mL). To the resulting mixture were added pyridine (252 mL, 3.11 mol) and DMAP (4-dimethylaminopyridine) (1.9 g, 15.6 mmol), and then added dropwise acetic anhydride (292 mL, 3.11 mol) in an ice-water bath. The reaction mixture was stirred at room temperature for 3 hr, quenched with water, and extracted with ethyl acetate (1.5 L). The organic layer was washed with a diluted hydrochloric acid for three times, with a saturated sodium bicarbonate for one time, with water, and with a saturated sodium chloride, dried over anhydrous sodium sulphate, and evaporated by rotation. The residue was recrystallized with ethanol to produce 81 g of a product in a yield of 42%.

(12) Preparation of (2S,3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol

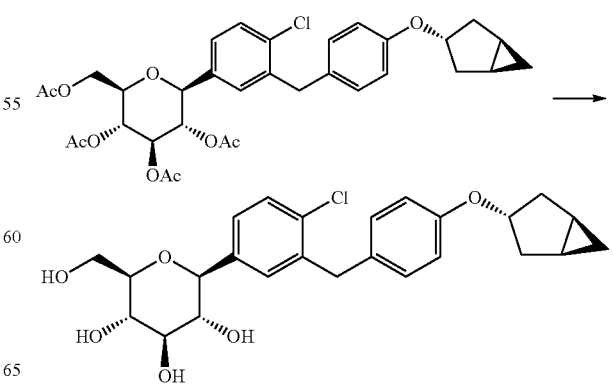

(2R,3R,4R,5S,6S)-2-(acetoxymethyl)-6-(3-(4-(((1R,3s,5S)-bicyclo[3.1.0]hexan-3-yl)oxy)benzyl)-4-chlorophenyl)tetrahydro-2H-pyran-3,4,5-triyl triacetate (81 g, 0.129 mol) was dissolved in a mixed solvent of tetrahydrofuran (313 mL), methanol (470 mL) and water (156 mL). To the resulting mixture was added lithium hydroxide monohydrate (6.32 g, 150 mmol). The mixture was stirred at room temperature overnight. TLC indicated the completion of reaction. The solvent was removed from the reaction mixture by rotary evaporation. The residual reaction mixture was dissolved with ethyl acetate (400 mL). The organic phase was washed with an aqueous saturated sodium chloride solution, with an aqueous KHSO$_4$ solution, and with water twice, dried over anhydrous sodium sulphate, and evaporated by rotation. The residue was purified with C18 reverse phase preparative chromatography to produce 54.2 g of a final product in a yield of 91%.

Formula: $C_{25}H_{29}ClO_6$ Mw: 460.95 LC-MS (m/z): 478.3 $[M+NH_4]^+$ $^1$H-NMR (400 MHz, MeOD) δ: 7.35-7.26 (m, 3H), 7.08-7.06 (d, 2H), 6.76-6.74 (d, 2H), 4.45-4.41 (m, 1H), 4.10-4.00 (m, 3H), 3.89-3.88 (d, 1H), 3.71-3.69 (m, 1H), 3.45-3.38 (m, 3H), 3.31-3.26 (m, 1H), 2.34-2.29 (m, 2H), 1.87-1.81 (m, 2H), 1.37-1.33 (m, 2H), 0.43-0.42 (m, 1H), 0.11-0.10 (m, 1H).

Example 2

Preparation of (2S,3R,4R,5S,6R)-2-(3-(4-(((1R,3r,5S)-bicyclo[3.1.0]hexan-3-yl)oxy)benzyl)-4-chlorophenyl)-6-(hydroxymethyl)tetrahydro-2H-pyran-3,4,5-triol (Formula III)

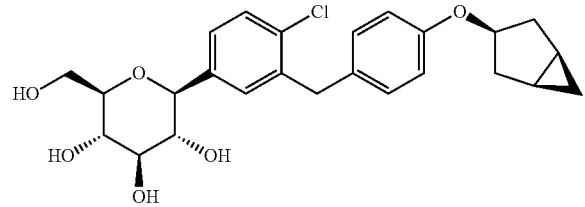 [SMILES: OC[C@H]1O[C@@H](c2ccc(Cl)c(Cc3ccc(O[C@@H]4C[C@@H]5C[C@@H]5C4)cc3)c2)[C@H](O)[C@@H](O)[C@@H]1O]

(1) Preparation of (1R,3r,5S)-3-(4-(5-bromo-2-chlorobenzyl)phenyloxy)bicyclo[3.1.0]hexane

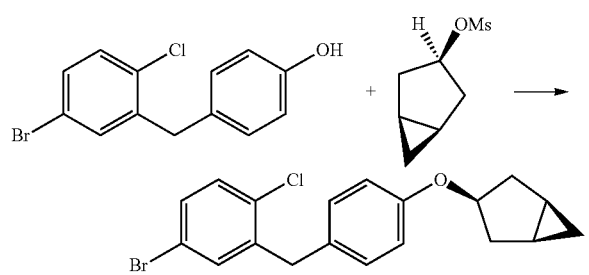

4-(5-bromo-2-chlorobenzyl)phenol (prepared according to steps (1)-(4) of Example 1) (29.7 g, 0.10 mol) was dissolved in toluene (450 mL). To the resulting mixture was successively added sodium hydroxide (8 g, 0.20 mol), water (27 mL), (1R,3r,5S)-bicyclo[3.1.0]hexan-3-yl methanesulfonate (prepared according to steps (5)-(6) of Example 1) (17.6 g, 0.10 mol), and benzyltriethylammonium chloride (1.05 g, 4.61 mmol). The mixture was reacted at 70° C. for 2 hr. TLC indicated the completion of reaction. The reaction mixture was extracted with ethyl acetate (500 mL). The organic phase was dried, and the solvent was collected by rotary evaporation. The residue was purified by a silica-gel column chromatography (petroleum ether:ethyl acetate=50:1) to produce 10.1 g of a product in a yield of 27%.

Formula: $C_{19}H_{18}BrClO$ Mw: 377.71

$^1$H-NMR (400 MHz, CDCl$_3$) δ: 7.28-7.21 (m, 3H), 7.07-7.05 (d, 2H), 6.76-6.72 (d, 2H), 4.79-4.76 (m, 1H), 3.98 (s, 2H), 2.22-2.16 (m, 2H), 2.05-2.01 (m, 2H), 1.35-1.31 (m, 2H), 0.62-0.58 (m, 1H), 0.51-0.46 (m, 1H).

(2) Preparation of (3R,4S,5S,6R)-2-(3-(4-(((1R,3r,5S)-bicyclo[3.1.0]hexan-3-yl)oxy)benzyl)-4-chlorophenyl)-6-(hydroxymethyl)-2-methoxytetrahydro-2H-pyran-3,4,5-triol

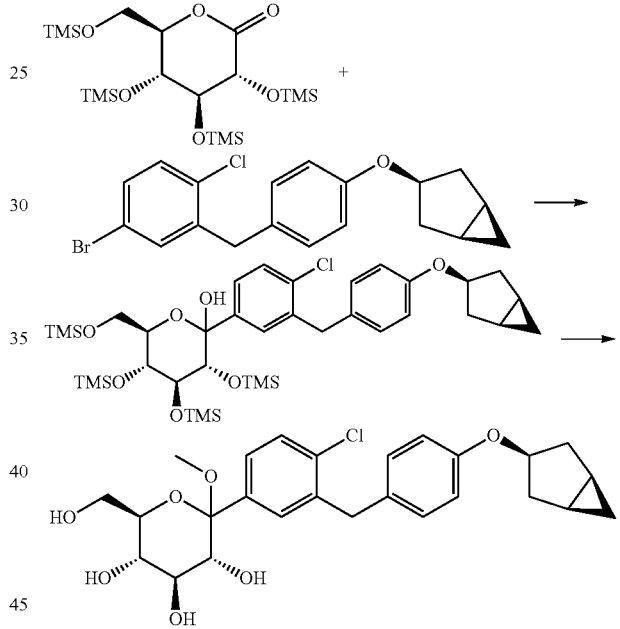

(1R,3r,5S)-3-(4-(5-bromo-2-chlorobenzyl)phenyloxy)bicyclo[3.1.0]hexane (1.5 g, 3.97 mmol) was dissolved in tetrahydrofuran (100 mL). The resulting mixture was cooled to −78° C. under a nitrogen protection. To the mixture was added dropwise n-butyl lithium (2 mL, 4.8 mmol). After the completion of dropwise addition, the resulting mixture was stirred at −78° C. for 1 hr. To the mixture was added dropwise a solution of (3R,4S,5R,6R)-3,4,5-tri((trimethylsilyl)oxy)-6-(((trimethylsilyl)oxy)methyl)tetrahydro-2H-pyran-2-one (3.0 g, 6.4 mmol) in toluene (25 mL). The resulting mixture was reacted for 1 h while the temperature was maintained at −78° C. Then to the reaction mixture was added a solution of methanesulfonic acid (3.8 g, 39.6 mmol) in methanol (50 mL). The resulting mixture was reacted for 0.5 hr while the temperature was maintained at −78° C., and then reacted at room temperature for 18 h. The reaction mixture was quenched with an aqueous saturated sodium bicarbonate solution (100 mL), and extracted with ethyl acetate (100 mL×3). The organic phases were combined, dried over anhydrous sodium sulphate, and filtered. The filtrate was concentrated under a reduced pressure to remove the solvent and produce 1.5 g of a product in a yield of 77%.

(3) Preparation of (3R,4R,5S,6R)-2-(3-(4-(((1R,3r,5S)-bicyclo[3.1.0]hexan-3-yl)oxy)benzyl)-4-chlorophenyl)-6-(hydroxymethyl)tetrahydro-2H-pyran-3,4,5-triol

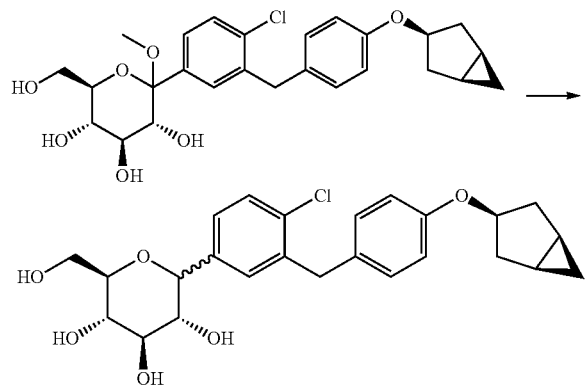

(3R,4S,5S,6R)-2-(3-(4-(((1R,3r,5S)-bicyclo[3.1.0]hexan-3-yl)oxy)benzyl)-4-chlorophenyl)-6-(hydroxymethyl)-2-methoxytetrahydro-2H-pyran-3,4,5-triol (1.40 g, 2.86 mmol) was dissolved in a mixed solution of methylene chloride (40 mL) and acetonitrile (40 mL). To the resulting mixture was added triethyl silane (1.0 g, 8.6 mmol). The mixture was stirred at room temperature, and boron trifluoride-diethyl etherate (1.2 g, 8.45 mmol) was added dropwise thereto. After the completion of addition, the resulting mixture was reacted at room temperature for 16 hr. To the reaction mixture was added an aqueous saturated sodium bicarbonate solution (100 mL). The resulting mixture was extracted with ethyl acetate (100 mL×3). The organic phases were combined, dried over anhydrous sodium sulphate, and filtered. The filtrate was concentrated under a reduced pressure to remove the solvent and produce 1.0 g of a crude product in a yield of 76%.

(4) Preparation of (2R,3R,4R,5S,6S)-2-(acetoxymethyl)-6-(3-(4-((1R,3r,5S)-bicyclo[3.1.0]hexan-3-yl)oxy)benzyl)-4-chlorophenyl)tetrahydro-2H-pyran-3,4,5-triyl triacetate

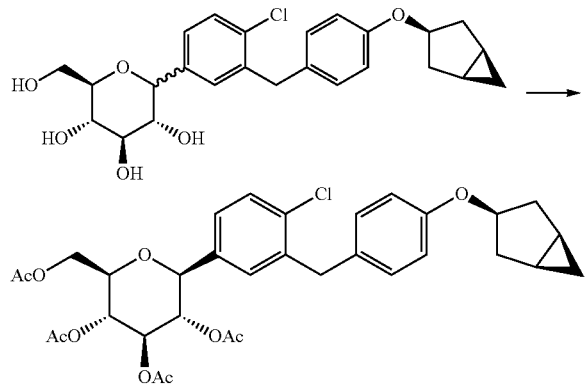

(3R,4R,5S,6R)-2-(3-(4-(((1R,3r,5S)-bicyclo[3.1.0]hexan-3-yl)oxy)benzyl)-4-chlorophenyl)-6-(hydroxymethyl)tetrahydro-2H-pyran-3,4,5-triol (1.0 g, 2.2 mmol) was dissolved in methylene chloride (40 mL). To the resulting mixture were added pyridine (1.76 mL) and DMAP (13 mg), and added dropwise acetic anhydride (2.07 mL) in an ice bath. The reaction mixture was stirred at room temperature for 3 hr, quenched with water (10 mL), and separated into an organic phase and an aqueous phase. The aqueous phase was extracted with ethyl acetate (50 mL×2). The organic phases were combined, dried over anhydrous sodium sulphate, purified by a silica-gel column chromatography (petroleum ether:ethyl acetate=2:1) to produce 400 mg of a product in a yield of 29%.

(5) Preparation of (2S,3R,4R,5S,6R)-2-(3-(4-(((1R,3r,5S)-bicyclo[3.1.0]hexan-3-yl)oxy)benzyl)-4-chlorophenyl)-6-(hydroxymethyl)tetrahydro-2H-pyran-3,4,5-triol

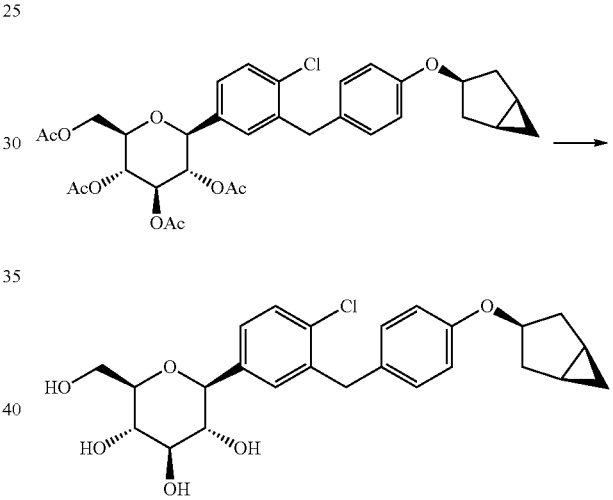

(2R,3R,4R,5S,6S)-2-(acetoxymethyl)-6-(3-(4-((1R,3r,5S)-bicyclo[3.1.0]hexan-3-yl)oxy)benzyl)-4-chlorophenyl)tetrahydro-2H-pyran-3,4,5-triyl triacetate (400 mg, 0.64 mmol) was dissolved in a mixed solvent of tetrahydrofuran (5 mL), water (5 mL) and methanol (5 mL). To the resulting mixture was added lithium hydroxide monohydrate (107.5 mg, 2.56 mmol). The reaction mixture was stirred at room temperature for 2 hr. TLC indicated the completion of reaction. The solvent was collected by rotary evaporation. The residue was purified by a silica-gel column chromatography (methylene chloride:methanol=10:1) to produce 200 mg of a final product in a yield of 68%.

Formula: $C_{25}H_{29}ClO_6$ Mw: 460.95

$^1$H-NMR (400 MHz, MeOD) d: 7.23-7.38 (m, 3H), 7.07 (m, 2H), 6.69 (m, 2H), 4.79 (m, 1H), 4.06-4.11 (m, 1H), 3.94-4.05 (m, 2H), 3.87 (m, 1H), 3.64-3.73 (m, 1H), 3.36-3.24 (m, 4H), 2.19 (m, 2H), 1.88-2.02 (m, 2H), 1.26-1.41 (m, 2H), 0.52-0.60 (m, 1H), 0.39-0.50 (m, 1H).

Example 3

Preparation of (2R,3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol (Formula IV)

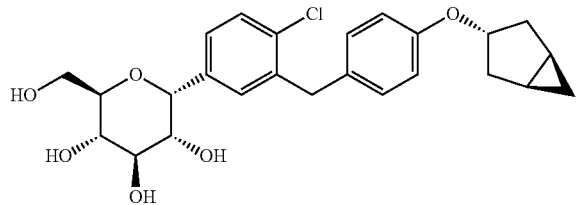 [SMILES: OC[C@H]1O[C@H](c2ccc(Cl)c(Cc3ccc(O[C@H]4C[C@@H]5C[C@@H]5C4)cc3)c2)[C@H](O)[C@@H](O)[C@@H]1O]

(1) Preparation of (3R,4S,5S,6R)-2-(3-(4-(((1R,3s,5S)-bicyclo[3.1.0]hexan-3-yl)oxy)benzyl)-4-chlorophenyl)-6-(hydroxymethyl)-2-methoxytetrahydro-2H-pyran-3,4,5-triol

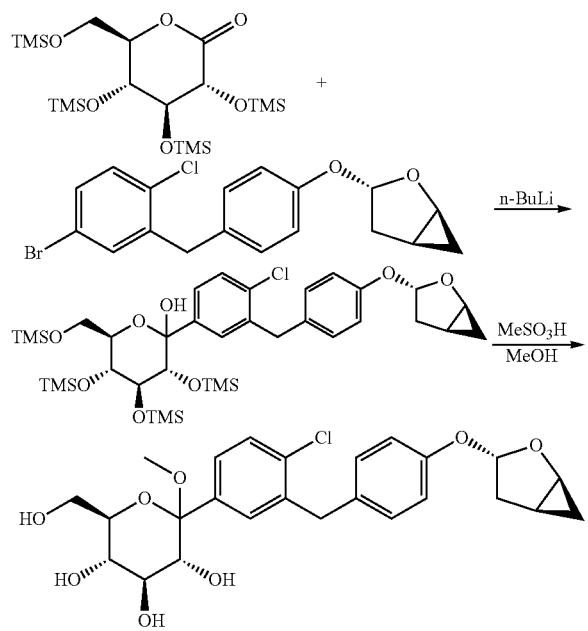

(1R,3s,5S)-3-(4-(5-bromo-2-chlorobenzyl)phenyloxy)bicyclo[3.1.0]hexane (5 g, 13.3 mmol) was dissolved in tetrahydrofuran (100 mL). The resulting mixture was cooled to −78° C. under a nitrogen protection. To the mixture was added dropwise n-BuLi (6.7 mL, 15.8 mmol). After the completion of dropwise addition, the resulting mixture was stirred at −78° C. for 1 hr. To the mixture was added dropwise a solution of (3R,4S,5R,6R)-3,4,5-tri((trimethylsilyl)oxy)-6-(((trimethylsilyl)oxy)methyl)tetrahydro-2H-pyran-2-one (10 g, 21.4 mmol) in toluene (50 mL). The resulting mixture was reacted for 1 h while the temperature was maintained at −78° C. Then to the reaction mixture was added a solution of methanesulfonic acid (12.7 g, 132 mmol) in methanol (60 mL). The resulting mixture was reacted at room temperature for 18 h. The reaction mixture was quenched with an aqueous saturated sodium bicarbonate solution (100 mL), and extracted with ethyl acetate (100 mL×3). The organic phases were combined, dried over anhydrous sodium sulphate, and filtered. The filtrate was concentrated under a reduced pressure to remove the solvent and produce 4.5 g of a product in a yield of 69%.

(2) Preparation of (3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol

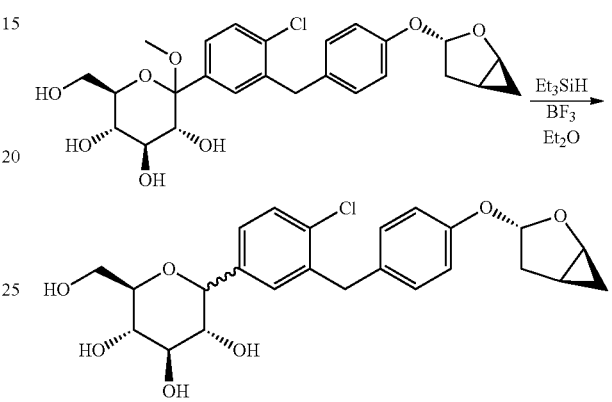

(3R,4S,5S,6R)-2-(3-(4-(((1R,3s,5S)-bicyclo[3.1.0]hexan-3-yl)oxy)benzyl)-4-chlorophenyl)-6-(hydroxymethyl)-2-methoxytetrahydro-2H-pyran-3,4,5-triol (4 g, 8.16 mmol) was dissolved in a mixed solution of methylene chloride (30 mL) and acetonitrile (30 mL). To the resulting mixture was added triethyl silane (2.86 g, 24.6 mmol). The mixture was stirred at room temperature, and boron trifluoride-diethyl etherate (3.43 g, 24.2 mmol) was added dropwise thereto. After the completion of addition, the resulting mixture was reacted at room temperature for 16 hr. To the reaction mixture was added an aqueous saturated sodium bicarbonate solution (50 mL). The resulting mixture was extracted with ethyl acetate (50 mL×3). The organic phases were combined, dried over anhydrous sodium sulphate, and filtered. The filtrate was concentrated under a reduced pressure to remove the solvent. The resulting crude product was purified with a silica-gel column chromatography (methylene chloride:methanol=10:1) to produce 2 mg of a product in a yield of 53%.

(3) Preparation of (2R,3R,4R,5S,6R)-2-(acetoxymethyl)-6-(3-(4-(((1R,3s,5S)-bicyclo[3.1.0]hexan-3-yl)oxy)benzyl)-4-chlorophenyl)tetrahydro-2H-pyran-3,4,5-triyl triacetate

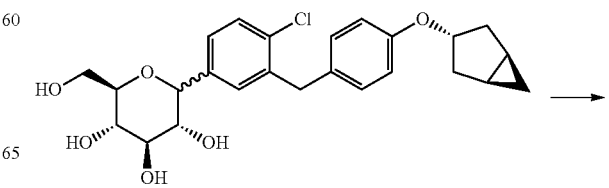

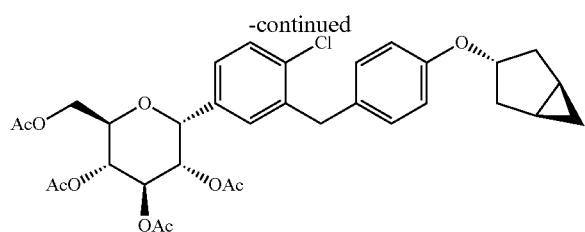

(3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol (1.0 g, 2.17 mmol) was dissolved in methylene chloride (20 mL). To the resulting mixture were added N,N-dIlsopropylethylamine (2.8 g, 21.7 mmol), acetic anhydride (2.2 g, 21.7 mmol) and a catalytic amount of 4-dimethylaminopyridine (25 mg). The reaction mixture was stirred at room temperature 2 hr, washed with 1N hydrochloric acid (15 mL), and separated into an organic phase and an aqueous phase. The organic phase was dried over anhydrous sodium sulphate, and filtered. The filtrate was concentrated under a reduced pressure to remove the solvent. The resulting crude product was purified with a silica-gel column chromatography (petroleum ether:ethyl acetate=5:1) to produce 0.55 g of a product in a yield of 40%.

(4) Preparation of (2R,3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol

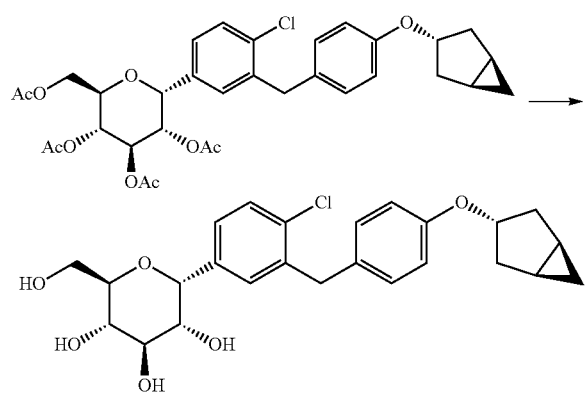

(2R,3R,4R,5S,6R)-2-(acetoxymethyl)-6-(3-(4-(((1R,3s,5S)-bicyclo[3.1.0]hexan-3-yl)oxy)benzyl)-4-chlorophenyl)tetrahydro-2H-pyran-3,4,5-triyl triacetate (0.55 g, 0.87 mmol) was dissolved in a mixed solvent of water, methanol and tetrahydrofuran (25 mL, 2:2:1). To the resulting mixture was added lithium hydroxide monohydrate (0.37 g, 8.7 mmol). The reaction mixture was stirred at room temperature overnight. The solvent was collected by rotary evaporation. The resulting mixture was extracted with ethyl acetate (10 mL×3). The organic phases were combined, dried over anhydrous sodium sulphate, and filtered. The filtrate was concentrated under a reduced pressure to remove the solvent. The resulting crude product was purified with a silica-gel column chromatography (methylene chloride:methanol=10:1) to produce 0.27 mg of a final product in a yield of 67.5%.

Formula: $C_{25}H_{29}ClO_6$ Mw: 460.95

$^1$H-NMR (400 MHz, MeOD) d: 7.21-7.31 (m, 3H), 6.93-7.09 (m, 2H), 6.74-6.79 (m, 2H), 4.53-4.63 (m, 1H), 4.39-4.48 (m, 1H), 4.14-4.20 (m, 1H), 3.89-4.11 (m, 5H), 3.82 (m, 1H), 3.67 (m, 1H), 2.32 (m, 2H), 1.84 (m, 2H), 1.34 (m, 2H), 0.43 (m, 1H), 0.10 (m, 1H).

Example 4

Preparation of (2R,3R,4R,5S,6R)-2-(3-(4-(((1R,3r,5S)-bicyclo[3.1.0]hexan-3-yl)oxy)benzyl)-4-chlorophenyl)-6-(hydroxymethyl)tetrahydro-2H-pyran-3,4,5-triol (Formula V)

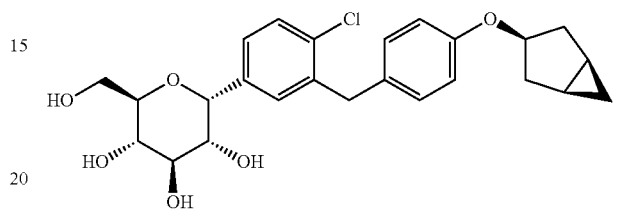

(1) Preparation of 2-chloro-5-iodobenzoyl chloride

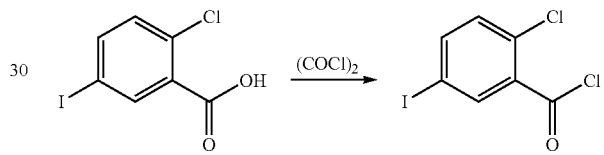

2-chloro-5-iodobenzoic acid (10.0 g, 35.5 mmol) was suspended in methylene chloride (200 mL). To the resulting mixture was added N,N-dimethylformamide (0.05 mL), and then added dropwise oxalyl chloride (11.3 g, 89.0 mmol) at 0° C. After the completion of dropwise addition, the resulting mixture was warmed up to room temperature and stirred for 4 hr. The resulting clear solution was evaporated by rotation to remove the solvent and produce 10.7 g of a product in a yield of 100%, which was directly used in the next reaction without purification.

(2) Preparation of (2-chloro-5-iodophenyl)(4-methoxyphenyl)methanone

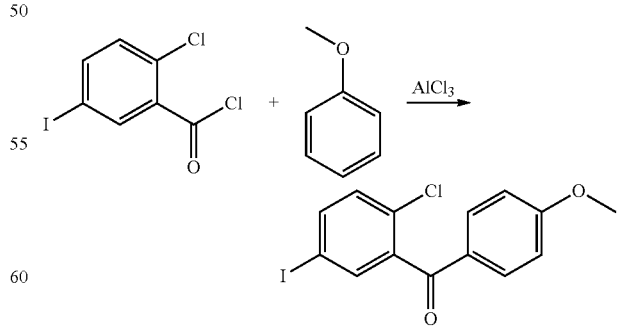

2-chloro-5-iodobenzoyl chloride (10.7 g, 35.5 mmol) was dissolved in methylene chloride (200 mL). The resulting mixture was cooled in an ice-water bath. To the mixture was added aluminum trichloride (10.4 g, 78.2 mmol), and then added dropwise a solution of anisole (4.2 g, 38.9 mmol) in methylene chloride (50 mL). After the completion of dropwise addition, the resulting mixture was warmed up to room temperature and stirred for 3 hr. The reaction mixture was poured into ice-water and quenched. To the reaction mixture was added 3 mol/L hydrochloric acid. The resulting mixture was separated into an aqueous phase and an organic phase. The aqueous phase was extracted with methylene chloride (150 mL×2). The organic phases were combined, washed with a saturated sodium chloride solution, dried over anhydrous sodium sulphate, and concentrated under a reduced pressure. The resulting crude product was purified with a silica-gel column chromatography (ethyl acetate:petroleum ether=0-1:100) to produce 12.0 g of a product in a yield of 91%.

(3) Preparation of 1-chloro-4-iodo-2-(4-methoxybenzyl)benzene

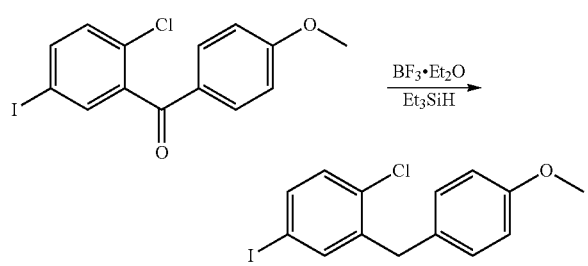

(2-chloro-5-iodophenyl)(4-methoxyphenyl)methanone (12.0 g, 32.2 mmol) and triethyl silane (9.86 g, 84.8 mmol) were dissolved in acetonitrile (200 mL). To the resulting mixture was added boron trifluoride-diethyl etherate complex (13.7 g, 96.5 mmol) at 0° C. After the completion of dropwise addition, the mixture was warmed up to 70° C., and stirred for 3 hr. Then the mixture was cooled to room temperature. The mixture was quenched with a saturated sodium bicarbonate solution, and extracted with ethyl acetate (200 mL×3). The organic phases were combined, washed with a saturated sodium chloride solution, dried over anhydrous sodium sulphate, and concentrated under a reduced pressure. The resulting crude product was purified with a silica-gel column chromatography (ethyl acetate: petroleum ether=0-1:100) to produce 10.0 g of a product in a yield of 87%.

(4) Preparation of 4-(2-chloro-5-iodobenzyl)phenol

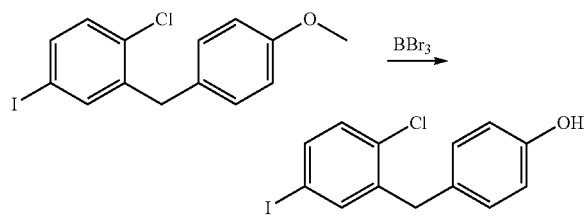

1-chloro-4-iodo-2-(4-methoxybenzyl)benzene (10.0 g, 27.9 mmol) was dissolved in methylene chloride (150 mL). To the resulting mixture was added dropwise boron tribromide (21 g, 83.7 mmol) under cooling in an ice-water bath. After the completion of dropwise addition, the mixture was warmed up to room temperature, and stirred for 3 hr. The mixture was quenched with a saturated sodium bicarbonate solution, was separated into an aqueous phase and an organic phase. The aqueous phase was extracted with methylene chloride (150 mL×2). The organic phases were combined, washed with a saturated sodium chloride solution, dried over anhydrous sodium sulphate, and concentrated under a reduced pressure. The resulting crude product was purified with a silica-gel column chromatography (ethyl acetate:petroleum ether=0-1:20) to produce 8.5 g of a product in a yield of 88%.

(5) Preparation of (4-(2-chloro-5-iodobenzyl)phenyloxy)tert-butyldimethylsilane

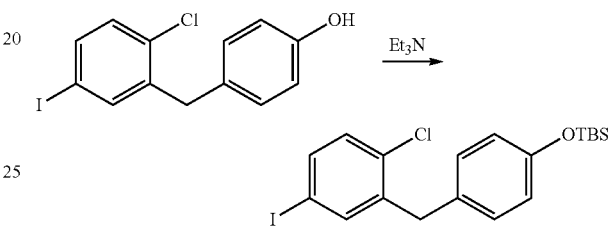

4-(2-chloro-5-iodobenzyl)phenol (8.5 g, 24.7 mmol) and triethylamine (5.0 g, 49.5 mmol) were dissolved in methylene chloride (200 mL). To the resulting mixture were added tert-butyldimethylsilane chloride (5.6 g, 37.1 mmol) and 4-(dimethylamino)pyridine (305 mg, 2.5 mmol) at 0° C. After the completion of addition, the mixture was warmed up to room temperature, and stirred for 18 hr. To the mixture was added water (100 mL). The resulting mixture was separated into an aqueous phase and an organic phase. The aqueous phase was extracted with methylene chloride (100 mL×2). The organic phases were combined, washed with a saturated aqueous sodium chloride solution, dried over anhydrous sodium sulphate, and concentrated under a reduced pressure. The resulting crude product was purified with a silica-gel column chromatography (ethyl acetate: petroleum ether=0-1:100) to produce 10.0 g of a product in a yield of 88%.

(6) Preparation of (3R,4S,5S,6R)-2-(3-(4-((tert-butyldimethylsilyl)oxy)benzyl)-4-chlorophenyl)-6-(hydroxymethyl)-2-methoxytetrahydro-2H-pyran-3,4,5-triol

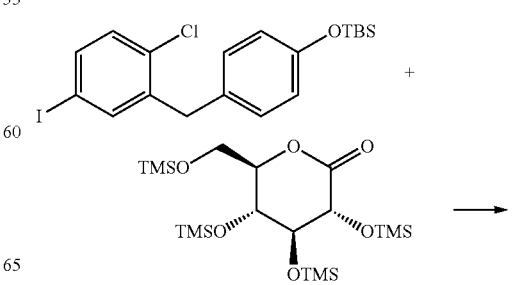

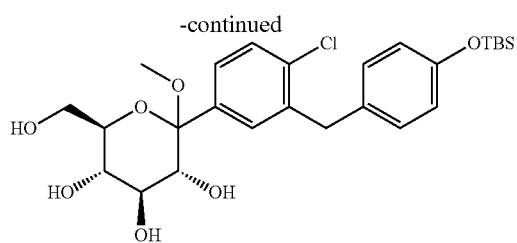

A solution of (4-(2-chloro-5-iodobenzyl)phenyloxy)tert-butyldimethylsilane (10.0 g, 21.8 mmol) in anhydrous tetrahydrofuran (80 mL) and toluene (80 mL) was cooled to −78° C. To the solution was slowly added dropwise a solution of n-butyl lithium in n-hexane (2.4 mol/L, 13.6 mL, 32.6 mmol). The resulting mixture was reacted at −78° C. for 2 hr, and then warmed up to −60° C. To the reaction mixture was added a solution of (3R,4S,5R,6R)-3,4,5-tri((trimethylsilyl)oxy)-6-(((trimethylsilyl)oxy)methyl)tetrahydro-2H-pyran-2-one (15.3 g, 32.7 mmol) in toluene (60 mL) in one batch. The resulting mixture was reacted at −60° C. for 2 hr. To the reaction mixture was added dropwise a solution of methanesulfonic acid (14.6 g, 152.1 mmol) in methanol (50 mL). After the completion of dropwise addition, the resulting mixture was reacted under stirring at room temperature for 17 hr. The reaction mixture was quenched with a saturated sodium bicarbonate solution, and separated into an aqueous phase and an organic phase. The aqueous phase was extracted with ethyl acetate (200 mL×3). The organic phases were combined, washed with a saturated sodium chloride solution, dried over anhydrous sodium sulphate, and concentrated under a reduced pressure to produce 9.0 g of a crude product, which was directly used in the next reaction without purification.

(7) Preparation of (3R,4S,5S,6R)-2-(4-chloro-3-(4-hydroxybenzyl)phenyl)-6-(hydroxymethyl)-2-methoxytetrahydro-2H-pyran-3,4,5-triol

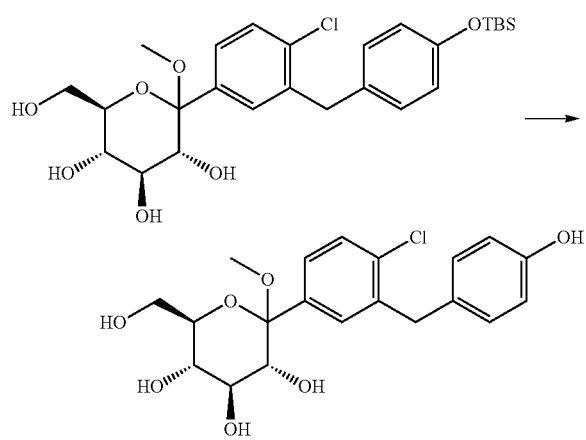

The crude (3R,4S,5S,6R)-2-(3-(4-((tert-butyldimethylsilyl)oxy)benzyl)-4-chlorophenyl)-6-(hydroxymethyl)-2-methoxytetrahydro-2H-pyran-3,4,5-triol (9.0 g) was dissolved in tetrahydrofuran (70 mL). To the resulting solution was added tetrabutyl ammonium fluoride trihydrate (22.1 g, 70 mmol). The resulting mixture was stirred at room temperature for 2 hr, and concentrated under a reduced pressure. To the mixture were added ethyl acetate (400 mL) and water (200 mL). The resulting mixture was separated into an aqueous phase and an organic phase. The organic phase was successively washed with water (200 mL×3) and a saturated sodium chloride solution, dried over anhydrous sodium sulphate, and concentrated under a reduced pressure to produce 6.5 g of a crude product, which was directly used in the next reaction without purification.

(8) Preparation of (3R,4R,5S,6R)-2-(4-chloro-3-(4-hydroxybenzyl)phenyl)-6-(hydroxymethyl)tetrahydro-2H-pyran-3, 4,5-triol

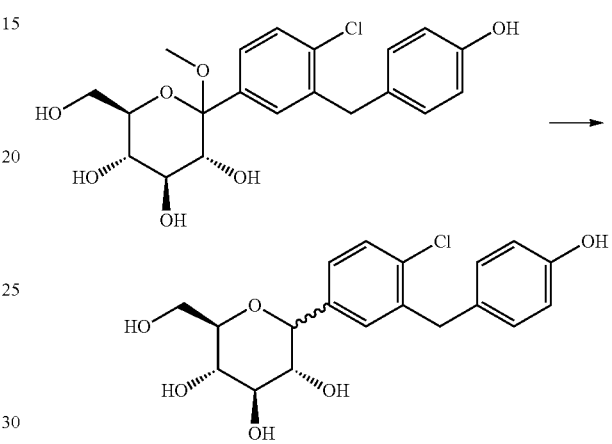

The crude (3R,4S,5S,6R)-2-(4-chloro-3-(4-hydroxybenzyl)phenyl)-6-(hydroxymethyl)-2-methoxytetrahydro-2H-pyran-3,4,5-triol (6.5 g) and triethyl silane (4.03 g, 34.7 mmol) were dissolved in a mixed solvent of methylene chloride (100 mL) and acetonitrile (100 mL). To the resulting mixture was added dropwise boron trifluoride-diethyl etherate complex (5.6 g, 39.5 mmol) at 0° C. After the completion of dropwise addition, the resulting mixture was warmed up to room temperature and stirred for 16 hr. The mixture was quenched with a saturated sodium bicarbonate solution, and extracted with ethyl acetate (250 mL×3). The organic phases were combined, washed with a saturated sodium chloride solution, dried over anhydrous sodium sulphate, and concentrated under a reduced pressure. The resulting crude product was purified with a silica-gel column chromatography (methanol:methylene chloride=0-1:15) to produce 3.8 g of a product in a yield of 46% (three steps in total).

(9) Preparation of (3R,4R,5S,6R)-2-(3-(4-(((1R,3r,5S)-bicyclo[3.1.0]hexan-3-yl)oxy)benzyl)-4-chlorophenyl)-6-(hydroxymethyl)tetrahydro-2H-pyran-3,4, 5-triol

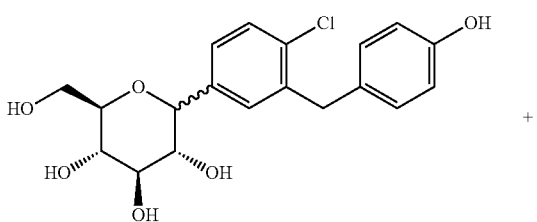

-continued

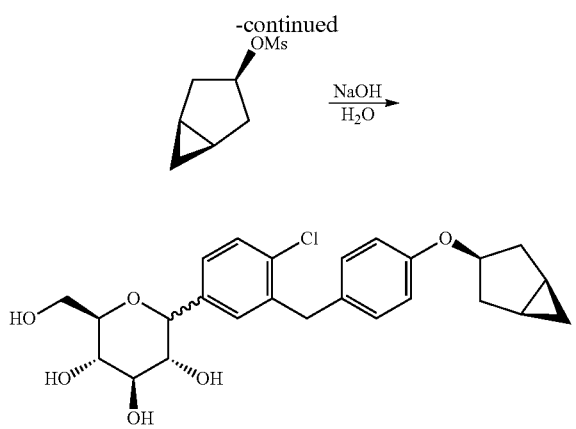

(3R,4R,5S,6R)-2-(4-chloro-3-(4-hydroxybenzyl)phenyl)-6-(hydroxymethyl)tetrahydro-2H-pyran-3, 4,5-triol (3.8 g, 10 mmol) and (1R,3r,5S)-bicyclo[3.1.0]hexan-3-yl methanesulfonate (3.5 g, 20 mmol) were suspended in toluene (100 mL) and water (10 mL). To the resulting suspension were successively added NaOH (1.0 g, 25 mmol) and benzyl triethylammonium chloride (114 mg, 0.5 mmol). The resulting mixture was heated to 80° C. and reacted for 16 hr. The reaction mixture was cooled to room temperature. To the reaction mixture was added water (50 mL). The resulting mixture was separated into an aqueous phase and an organic phase. The aqueous phase was extracted with ethyl acetate (50 mL×3). The organic phases were combined, washed with a saturated sodium chloride solution, dried over anhydrous sodium sulphate, and concentrated under a reduced pressure to produce 5.0 g of a crude product, which was directly used in the next reaction without purification.

(10) Preparation of (2R,3R,4R,5S,6R)-2-(acetoxymethyl)-6-(3-(4-(((1R,3r,5S)-bicyclo[3.1.0]hexan-3-yl)oxy)benzyl)-4-chlorophenyl)tetrahydro-2H-pyran-3,4,5-triyl triacetate

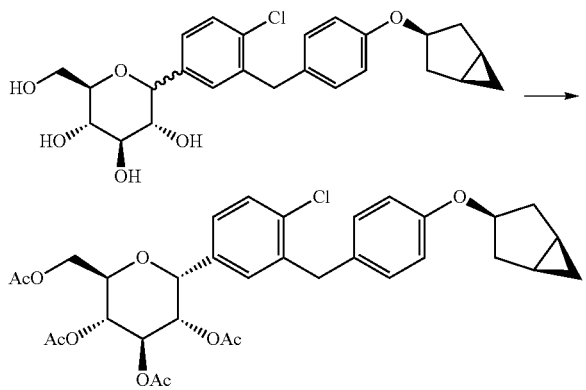

The crude (3R,4R,5S,6R)-2-(3-(4-(((1R,3r,5S)-bicyclo[3.1.0]hexan-3-yl)oxy)benzyl)-4-chlorophenyl)-6-(hydroxymethyl)tetrahydro-2H-pyran-3,4,5-triol (5.0 g) was dissolved in methylene chloride (50 mL). To the resulting mixture were added pyridine (7.9 g, 100 mmol) and 4-(dimethylamino)pyridine (122 mg, 1 mmol), and then added acetic anhydride (10.2 g, 100 mmol) in an ice bath. The mixture was warmed up to room temperature and stirred for 4 hr. To the mixture was added water. The resulting mixture was extracted with ethyl acetate (150 mL×3). The organic phases were combined, washed successively with 1 mol/L hydrochloric acid (150 mL×3), a saturated sodium bicarbonate solution (150 mL) and a saturated sodium chloride solution, dried over anhydrous sodium sulphate, and concentrated under a reduced pressure. The resulting crude product was purified with a silica-gel column chromatography (ethyl acetate:petroleum ether=0-1:4) to produce 350 mg of a product in a yield of 5.6% (two steps in total).

(11) Preparation of (2R,3R,4R,5S,6R)-2-(3-(4-(((1R,3r,5S)-bicyclo[3.1.0]hexan-3-yl)oxy)benzyl)-4-chlorophenyl)-6-(hydroxymethyl)tetrahydro-2H-pyran-3,4,5-triol

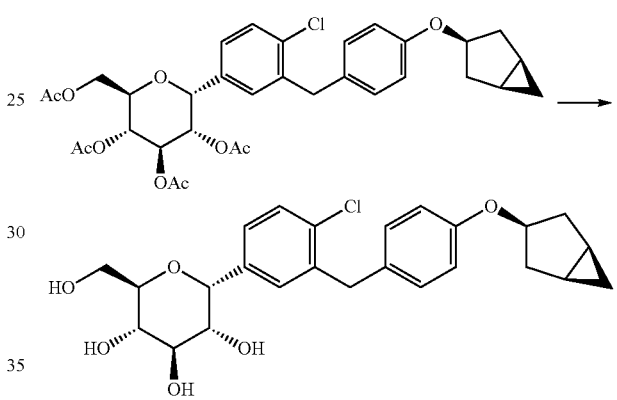

(2R,3R,4R,5S,6R)-2-(acetoxymethyl)-6-(3-(4-(((1R,3r,5S)-bicyclo[3.1.0]hexan-3-yl)oxy)benzyl)-4-chlorophenyl)tetrahydro-2H-pyran-3,4,5-triyl triacetate (350 mg, 0.56 mmol) was dissolved in a mixed solvent of water, methanol and tetrahydrofuran (1:2:2, 25 mL). To the resulting mixture was added LiOH.H$_2$O (118 mg, 2.8 mmol). The reaction mixture was stirred at room temperature for 16 hr, and concentrated under a reduce pressure. To the resulting concentrate was water (20 mL). The resulting mixture was extracted with ethyl acetate (30 mL×3). The organic phases were combined, washed with a saturated sodium chloride solution, dried over anhydrous sodium sulphate, and concentrated under a reduced pressure. The resulting crude product was purified with a silica-gel column chromatography (methanol:methylene chloride=0-1:15) to produce 140 mg of a product in a yield of 54.7%.

Formula: $C_{25}H_{29}ClO_6$ Mw: 460.95

$^1$H-NMR (400 MHz, MeOD) δ: 7.29-7.31 (m, 3H), 7.04-7.07 (m, 2H), 6.68-6.71 (m, 2H), 4.77-4.81 (m, 1H), 4.57-4.61 (m, 1H), 4.15-4.19 (m, 1H), 3.98-4.05 (4H, m), 3.92-3.93 (m, 1H), 3.80-3.83 (m, 1H), 3.63-3.68 (m, 1H), 2.16-2.21 (m, 2H), 1.94-1.97 (m, 2H), 1.24-1.34 (m, 2H), 0.54-0.56 (m, 1H), 0.39-0.49 (m, 1H).

The invention claimed is:
1. An intermediate for the compound represented by formula (II),

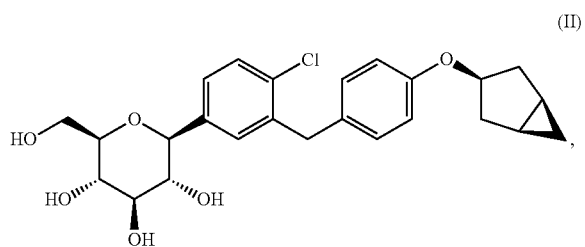 [SMILES: OC[C@H]1O[C@@H](c2ccc(Cl)c(Cc3ccc(O[C@@H]4C[C@@H]5C[C@@H]5C4)cc3)c2)[C@H](O)[C@@H](O)[C@@H]1O]

(II)

which is (2S,3R,4R,5S,6R)-2-(3-(4-(((1R,3s,5S)-bicyclo[3.1.0]hexan-3-yl)oxy)benzyl)-4-chlorophenyl)-6-(hydroxymethyl)tetrahydro-2H-pyran-3,4,5-triol,
wherein said intermediate is

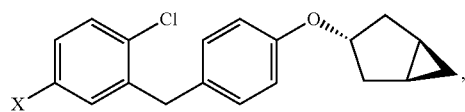

wherein X represents bromo or iodo.

2. An intermediate for the compound represented by formula (III),

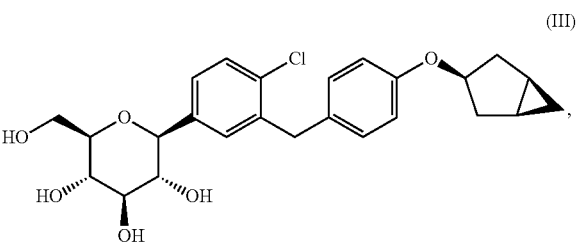 [SMILES: OC[C@H]1O[C@@H](c2ccc(Cl)c(Cc3ccc(O[C@@H]4C[C@@H]5C[C@@H]5C4)cc3)c2)[C@H](O)[C@@H](O)[C@@H]1O]

(III)

(III), which is (2S,3R,4R,5S,6R)-2-(3-(4-(((1R,3r,5S)-bicyclo[3.1.0]hexan-3-yl)oxy)benzyl)-4-chlorophenyl)-6-(hydroxymethyl)tetrahydro-2H-pyran-3,4,5-triol,
wherein said intermediate is

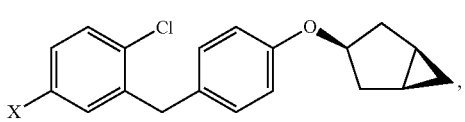

wherein X represents bromo or iodo.

* * * * *